(12) United States Patent
Chow et al.

US008557853B2

(10) Patent No.: US 8,557,853 B2
(45) Date of Patent: Oct. 15, 2013

(54) ARYL FLUOROETHYL UREAS ACTING AS ALPHA 2 ADRENERGIC AGENTS

(75) Inventors: Ken Chow, Newport Coast, CA (US); Wenkui K. Fang, Irvine, CA (US); Evelyn G. Corpuz, Irvine, CA (US); Daniel W. Gil, Corona Del Mar, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/950,667

(22) Filed: Dec. 5, 2007

(65) Prior Publication Data

US 2008/0194650 A1 Aug. 14, 2008

Related U.S. Application Data

(60) Provisional application No. 60/888,966, filed on Feb. 9, 2007.

(51) Int. Cl.
*A61K 31/44* (2006.01)
*C07D 213/62* (2006.01)
*C07D 211/82* (2006.01)

(52) U.S. Cl.
USPC ............................ 514/357; 546/300; 546/332

(58) Field of Classification Search
USPC ................................... 546/300, 332; 514/357
See application file for complete search history.

(56) References Cited

U.S. PATENT DOCUMENTS

| 2,711,428 | A | 6/1955 | Goodson et al. | |
|---|---|---|---|---|
| 4,803,223 | A * | 2/1989 | Kato | 514/521 |
| 6,797,823 | B1 * | 9/2004 | Kubo et al. | 544/287 |
| 2007/0270498 | A1 * | 11/2007 | Chow et al. | 514/595 |

OTHER PUBLICATIONS

Hcaplus Abstract 2002:314913, (2002).*
Patani et. al., "Bioisosterism: A Rational Approach in Drug Design", Chem. Rev. 1996, 3147-3176.*
Hcaplus 1967:1279, "Synthesis of potential anticancer agents. XXXVI. n-nitrosoureas. 2. Haloalkyl derivatives", Johnston et. al., 1966.*
Patani et. al, "Bioisosterism: A Rational Approach in Drug Design", Chem. Rev. 1996, pp. 3147-3176.*
Hcaplus 2000:513673, "Preparation and anti-tumor, anti-atherosclerosis, anti-psoriasis, anti-diabetes, and anti-arthritis activities of quinolines and quinazolines", Kubo et. al., 2000.*
Hcaplus 2002:314913, "Preparation of urea derivatives containing nitrogenous aromatic ring compounds as inhibitors of angiogenesis", Funahashi et. al., 2002.*
Patani et. al., "Bioisosterism: A Rational Approach in Drug Design", Chem. Rev. 1996, pp. 3147-3178.*
Hcaplus 1967: 1279, "Synthesis of potential anti-cancer agents. XXXVI. N-nitrosureas. 2. Haloalkyl derivatives", Johnston et. al., 1966.*
Johnston, T. et al., J. Med. Chem. 1966, vol. 9, pp. 892-910.*
Robert R. Ruffolo, Jr., α-Adrenoreceptors: Molecular Biology, Biochemistry and Pharmacology, (Progress in Basic and Clinical Pharmacology series, Karger, 1991).
Messier et. Al., 1995, Pharmacol. Toxicol. 76, pp. 308-311.
Nahm et al, "N-Methoxy-N-Methylamides As Effective Acylating Agents", *Tet. Letters*, 22, 3815-3818, 1981.
Jenkins, S., "The Grignard Reaction in the Synthesis of Ketones. I. A New Method of Preparing Desoxybenzoins", *J. Am. Chem. Soc.*, 55, 703-706, 1933.
Jenkins et al, "The Grignard Reaction in the Synthesis of Ketones. II. The Preparation of a Series of Mono-and Di-chlorodesoxybenzoins", *J. Am. Chem. Soc.*, 55, 1618-1621,1933.
Moffett et al, "Central Nervous System Agents. 4.[1] Analogs of 3-Amino-2-phenylpropiophenone", *J. Med. Chem.*, 15, 1243-1247, 1972.
Schneider et al, "1,1,2-Triphenylbut-1-enes: Relationship between Structure, Estradiol Receptor Affinity, and Mammary Tumor Inhibiting Properties", *J. Med. Chem.*, 25, 1070-1077, 1982.
Callahan, et al., "Identification of Novel Inhibitors of the Transforming Growth Factor •1 (TGF-•1) Type 1 Receptor (ALK5)" *J. Med. Chem.*, 45, 999-1001, 2002.
Hashimoto et al, "4-(4-Cycloalkyl/aryl-oxazol . . . " *J. Med. Chem.*, 45, 1511-1517, 2002.
Gyenes et al, "Convenient Access to Primary Amines by Employing the Barbier-Type Reaction of N-(Trimethylsilyl)imines Derived from Aromatic and Aliphatic Aldehydes", *J. Org. Chem.*, 63, 2824-2828, 1998.
Cooper et al, "Cytotoxic Compounds. Part VII.1 α-Aryl-α-halogenoacetophenones, their Enol Acetates, and Some Related Compounds", *J. Chem. Soc. C*, 533-540, 1966.
Anstead et al, "Torsionally and Hydrophobically Modified 2,3-Diarylindenes as Estrogen Receptor Ligands", *J. Med. Chem.*, 33, 2726-2734, 1990.
Turnbull et al, "The Sydnone Ring as an ortho-Director of Lithiation. 2.1 Dilithiation of 3-Phenylsydnone and Regiospecific o-Aryl Acylation Using N-methoxy-N-methylamides", *Tetrahedron Lett.*, 39, 1509-1512, 1998.
Jenkins, S., "Benzoin Reduction I. The Mechanism of Ketone Formation. The Case of Benzanisoin", *J. Am. Chem. Soc.*, 54, 1155-1161, 1932.
Gee et al.,"10,5-(Iminomethano)-10,11-dihydro-5H-dibenzo[a,d]cycloheptane and Derivatives. Potent PCP Receptor Ligands",J. Med. Chem., 36, 1938-1946, 1993.
Gallagher et al., "Regulation of Stress-Induced Cytokine Production by Pyridinylimidazoles; Inhibition of CSBP Kinase" Bioorg. Med. Chem., 5, 49-64, 1997.
Kawase et al, "Synthetic Studies on the Benzofuran . . . " Bull. Chem. Soc. Jpn., 31, 691,1958.
Clader, et al., "Susbsituted (1,2-Diarylethyl)amide Acyl-CoA:Cholesterol Acyltransferase Inhibitors: Effect of Polar Groups on in Vitro and in Vivo Activity", J. Med. Chem. 1995, 38, 1600-1607.
Christy et al., "2-,3-, and 4-(α,α,β,β-Tetrafluorophenethyl)benzylamines. A New Class of Antiarrhythmic Agents1", J. Med. Chem., 20, 421-430, 1977.

(Continued)

*Primary Examiner* — Janet L Andres
*Assistant Examiner* — Heidi Reese
(74) *Attorney, Agent, or Firm* — John E. Wurst; Allergan, Inc.

(57) ABSTRACT

The invention provides well-defined aryl fluoroethyl ureas that are useful as selective alpha$_2$ adrenergic agonists. As such, the compounds described herein are useful in treating a wide variety of disorders associated with modulation of alpha$_2$ adrenergic receptors.

6 Claims, No Drawings

(56) References Cited

OTHER PUBLICATIONS

Karaman et al, "A Novel N-Dealkylation Reaction of N, N-Dialkylarylcarboxamies Promoted by Electron Transfer From Alkali Metals", Tetrahedron Lett., 31, 941-944, 1990.

Ottosen et al, "Synthesis and Structure-Activity Relationship of Aminobenzophenones. A Novel Class of p38 MAP Kinase Inhibitors with High Antiinflammatory Activity", J. Med. Chem., 46, 5651-5662, 2003.

Otter et al, "Benzopyrylium Salts. V. Preparation and Properties of Substituted 2,3-Dephenylbenzopyrylium Perchlorates", J. Am. Chem. Soc., 73, 887-888, 1951.

Dainippon Pharm.; BE 845638; Chem.Abstr. 88, 22977, 1977.

Inaba et al, "Metallic Nickel-Mediated Synthesis of Ketones by the Reaction of Benzylic, Allylic, Vinylic, and Pentafluorophenyl Halides with Acid Halides", J. Org. Chem., 50, 1373-1381, 1985.

Ghosh et al, 1,2-Diphenylethylamines as Potential Non-stimulant Anorectics, Arzneim. Forsch., 28, 1561-1564, 1978.

Selikson et al, "The Oxidative Decyanation of Secondary Nitriles via α-Hydroperoxynitriles", J. Org. Chem., 40, 267-268, 1975.

Sternbach et al., "Quinazolines and 1,4-Benzodiazepines. V. o-Aminobenzophenones", J. Org. Chem., 27, 3781-3786, 1962.

Fischer et al., "The Acid-catalysed Bromination of Substituted Benzyl Phenyl Ketones", J. Chem. Soc., 3318-3319, 1962.

Ott, Phenyl-2-Thienylglycolic- . . . Org. Synth. Isotopes, 152-155, 1958.

Hill et al, "Preparation of Some α-(2-Thienyl)-β-arylethylamines1" Org. Chem., 23, 1289-1290, 1958.

Hecht, S.S. et al., "Synthesis and Mutagenicity of Modified Chrysenes Related to the Carcinogen, 5-Methylchrysene1", J. Med. Chem., 21, 38-44, 1978.

Stefanidis et al, "Rate-Equilibrium Relationships for the Deprotonation of 4-Phenacylpyridines and 4-Phenacylpyridinium Cations", J. Am. Chem. Soc., 112, 3163-3168, 1990.

Dankova et al., Zh. Obshch. Khim. 1951, 21, 787-795; engl. pp. 867-875.

Fontana et al, "Equilibrium Constants for Ionisation and Enolisation of 2-Phenylacetylfuran", J. Chem. Soc. Perkin Trans. 2, 12, 2453-2460, 1994.

Demir et al, "Novel Enantioselective Synthesis of Both Enantiomers of Furan-2-yl Amines and Amino Acids", Acta, 86, 91-105, 2003.

Kolehmainen et al, "Substituent and temperature controlled tautomerism of 2-phenacyl- . . ."J. Chem. Soc. Perkin Trans. 2, 11, 2185-2191, 2000.

\* cited by examiner

ARYL FLUOROETHYL UREAS ACTING AS ALPHA 2 ADRENERGIC AGENTS

RELATED APPLICATION

This application claims the benefit of U.S. Provisional Application Ser. No. 60/888,966, filed Feb. 9, 2007.

FIELD OF THE INVENTION

The present invention relates generally to aryl fluoroethyl ureas and to their use as agonists, for example as specific or selective agonists of alpha$_2$ adrenergic receptors. The invention relates specifically to the use of these compounds and pharmaceutical compositions containing these compounds to treat disorders associated with alpha$_2$ adrenergic receptor modulation.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the α-adrenergic receptors, the reader's attention is directed to Robert R. Ruffolo, Jr., α-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting α-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

SUMMARY OF THE INVENTION

The invention provides well-defined aryl fluoroethyl ureas that are useful as selective alpha$_2$ adrenergic agonists. As such, the compounds described herein are useful in treating a wide variety of disorders associated with modulation of alpha$_2$ adrenergic receptors.

In one embodiment of the invention, there are provided compounds having the structure

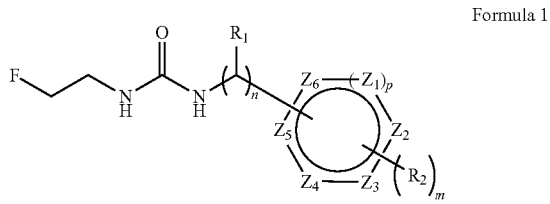

Formula 1 or pharmaceutically acceptable salts thereof
wherein:
$R_1$ is H, alkyl, phenyl, or substituted phenyl;
n is 0 or 1;
$Z_1$-$Z_6$ are each independently C, CH, N, O, or S;
p is 0 or 1;
m is 0 to 5;
each $R_2$ is independently H, lower alkyl, halide, trifluoromethyl, lower alkenyl, lower alkynyl, cycloalkyl, —CN, —CH$_2$CN, —CH$_2$SR$_3$, —CH$_2$N(R$_3$)$_2$, —CH$_2$OR$_3$, —OR$_3$, —SR$_3$, —N(R$_3$)$_2$, —C(O)R$_4$;
wherein two $R_2$ moieties taken together with carbon atoms to which each $R_2$ is attached may form an aryl, substituted aryl, heteroaryl, substituted heteroaryl, cycloalkyl, substituted cycloalkyl, heterocyclic, or substituted heterocyclic ring;
each $R_3$ is independently H, lower alkyl, cycloalkyl, allyl, phenyl, substituted phenyl, heteroaryl, or substituted heteroaryl; and
each $R_4$ is independently H, lower alkyl, cycloalkyl, alkoxy, phenyl, substituted phenyl, heteroaryl, substituted heteroaryl, or trifluoromethyl.

In another embodiment, there are provided pharmaceutical compositions including at least one aryl fluoroethyl urea of the invention in a pharmaceutically acceptable carrier therefor.

In a further embodiment of the invention, there are provided methods for treating disorders associated with modulation of alpha$_2$ adrenergic receptors. Such methods can be performed, for example, by administering to a subject in need thereof a pharmaceutical composition containing a therapeutically effective amount of at least one aryl fluoroethyl urea of the invention.

In still another embodiment of the invention, there are provided methods for treating disorders associated with modulation of alpha$_2$ adrenergic receptors. Such methods can be performed for example, by administering to a subject in need thereof a therapeutically effective amount of at least one aryl fluoroethyl urea of the invention, or any combination thereof, or pharmaceutically acceptable salts, hydrates, solvates, crystal forms and individual isomers, enantiomers, and diastereomers thereof.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)R$_5$, —CH$_2$OR$_5$, —C(O)—, —C(O)—, —S—, —S(O)$_2$, —OC(O)—O—, wherein R$_5$ is H or lower alkyl, acyl, oxyacyl, carboxyl, carbamate, sulfonyl, sulfonamide, sulfuryl.

As used herein, "lower alkyl" refers to alkyl moieties having from 1 to about 6 carbon atoms.

As used herein, "alkenyl" refers to straight or branched chain hydrocarbyl groups having at least one carbon-carbon double bond, and having in the range of 2 up to about 100 carbon atoms, and "substituted alkenyl" refers to alkenyl groups further bearing one or more substituents as set forth above. As used herein, "lower alkenyl" refers to alkenyl moieties having from 2 to about 6 carbon atoms.

As used herein, "alkynyl" refers to straight or branched chain hydrocarbyl groups having at least one carbon-carbon triple bond, and having in the range of 2 up to about 100 carbon atoms, and "substituted alkynyl" refers to alkynyl groups further bearing one or more substituents as set forth above. As used herein, "lower alkynyl" refers to alkynyl moieties having from 2 to about 6 carbon atoms.

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). "Substituted heteroaryl" refers to heteroaryl groups further bearing one or more substituents as set forth above.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms. "Substituted heterocyclic" refers to heterocyclic groups further bearing one or more substituents as set forth above.

As used herein, "halogen" or "halide" refers to fluoride, chloride, bromide or iodide.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The invention provides compounds having the structure:

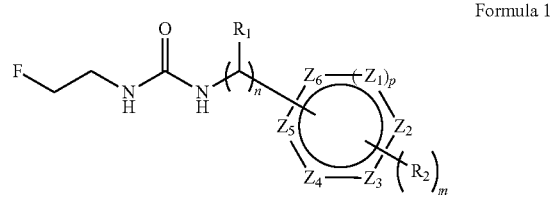

Formula 1 or pharmaceutically acceptable salts thereof
wherein:
R$_1$ is H, alkyl, phenyl, or substituted phenyl;
n is 0 or 1;
Z$_1$-Z$_6$ are each independently C, CH, N, O, or S;
p is 0 or 1;
m is 0 to 5;
each R$_2$ is independently H, lower alkyl, halide, trifluoromethyl, lower alkenyl, lower alkynyl, cycloalkyl, —CN, —CH$_2$CN, —CH$_2$SR$_3$, —CH$_2$N(R$_3$)$_2$, —CH$_2$OR$_3$, —OR$_3$, —SR$_3$, —N(R$_3$)$_2$, —C(O)R$_4$;

wherein two R$_2$ moieties taken together with carbon atoms to which each R$_2$ is attached may form an aryl, substituted aryl, heteroaryl, substituted heteroaryl, cycloalkyl, substituted cycloalkyl, heterocyclic, or substituted heterocyclic ring;

each R$_3$ is independently H, lower alkyl, cycloalkyl, allyl, phenyl, substituted phenyl, heteroaryl, or substituted heteroaryl; and each R$_4$ is independently H, lower alkyl, cycloalkyl, alkoxy, phenyl, substituted phenyl, heteroaryl, substituted heteroaryl, or trifluoromethyl.

In some embodiments of the invention, there are provided aryl fluoroethyl ureas according to Formula 1 wherein p is 1 and each of Z$_1$ to Z$_6$ is carbon.

In other embodiments of the invention, there are provided aryl fluoroethyl ureas according to Formula 1 wherein m is at least one, and each R$_2$ is independently —H, lower alkyl, halide, trifluoromethyl, or —OR$_3$.

Exemplary compounds according to these embodiments of the invention include, but are not limited to, compounds having the structure:

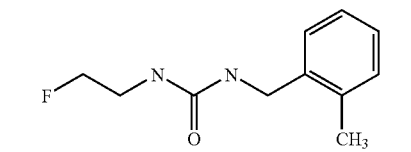

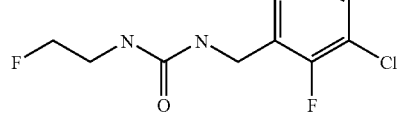

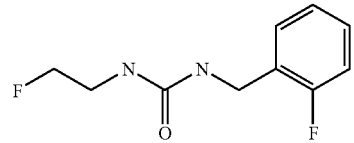

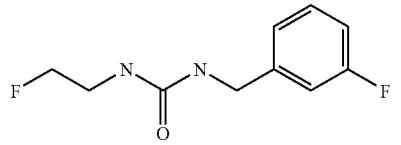

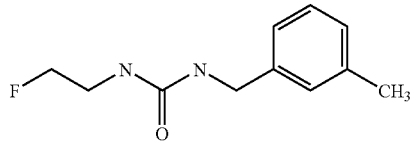

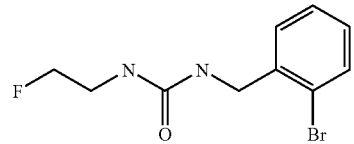

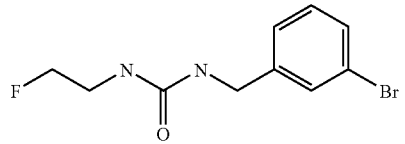

-continued

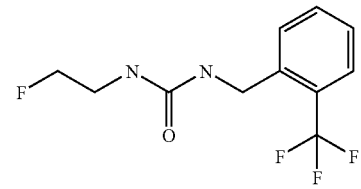

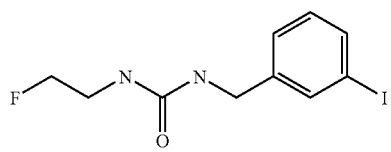

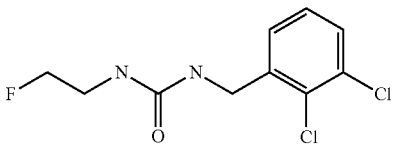

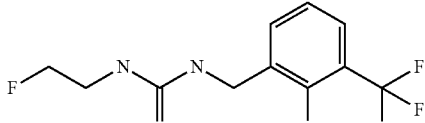

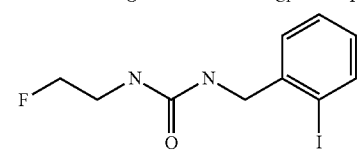

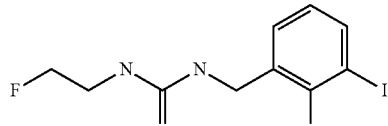

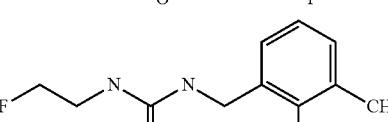

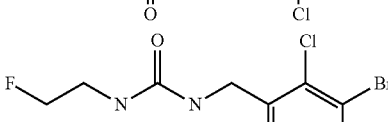

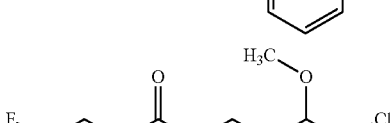

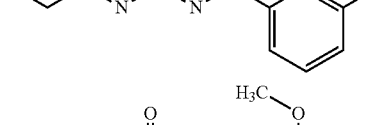

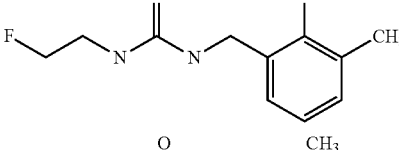

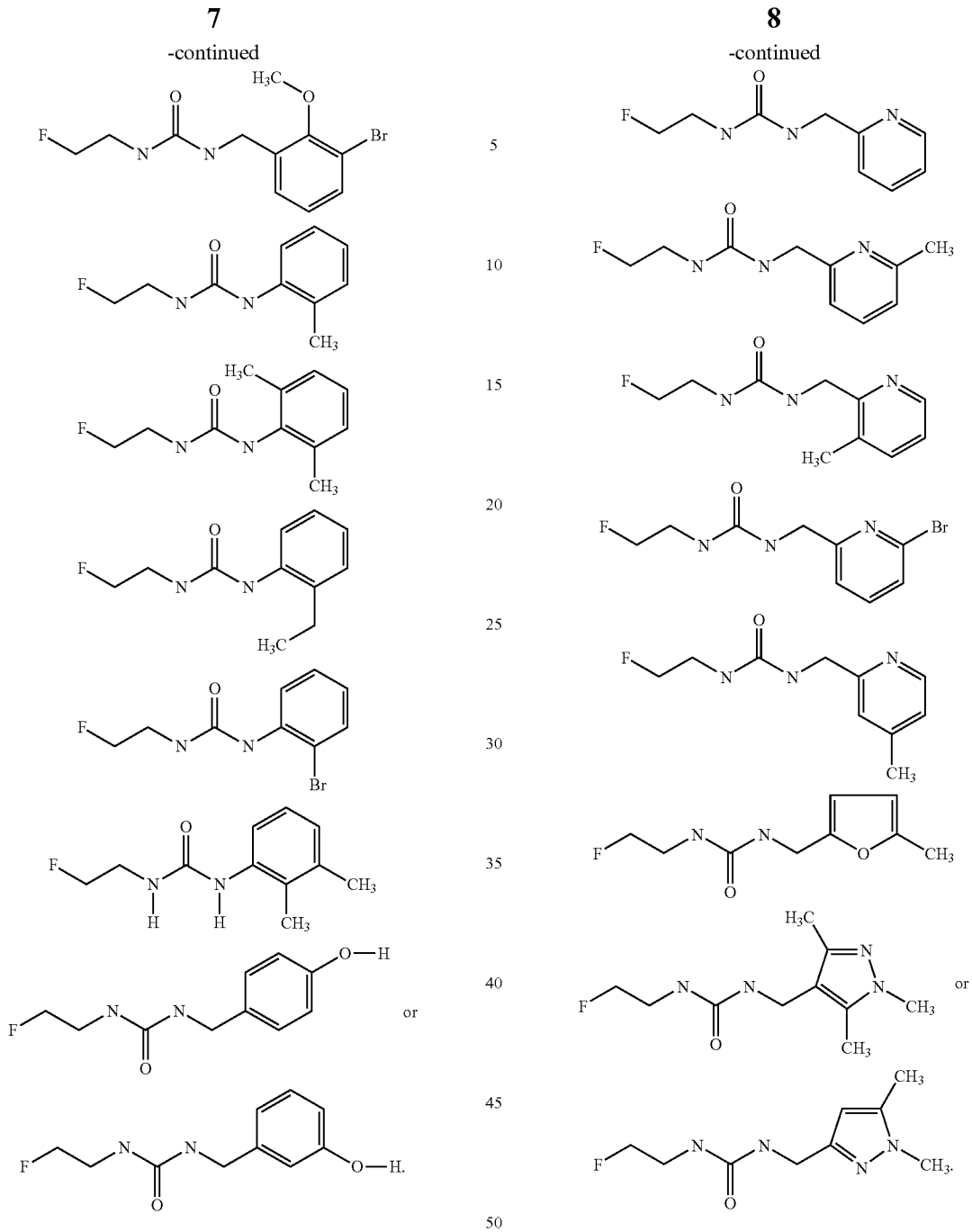

In further embodiments of the invention, there are provided aryl fluoroethyl ureas according to Formula 1 wherein at least one of $Z_1$ to $Z_6$ is N, O, or S. Exemplary compounds according to these embodiments of the invention include, but are not limited to, compounds having the structure:

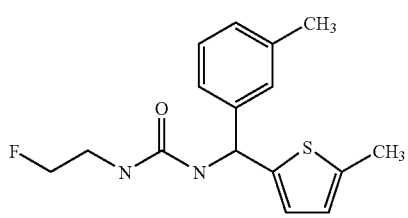

In other embodiments of the invention, there are provided aryl fluoroethyl ureas according to Formula 1 wherein m is 2 and each $R_2$ taken together with the carbon atoms to which each $R_2$ is attached forms an aryl, substituted aryl, heteroaryl, substituted heteroaryl, cycloalkyl, substituted cycloalkyl, heterocyclic, or substituted heterocyclic ring. Exemplary compounds according to these embodiments of the invention include, but are not limited to, compounds having the structure:

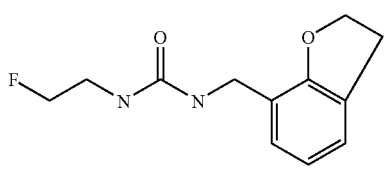

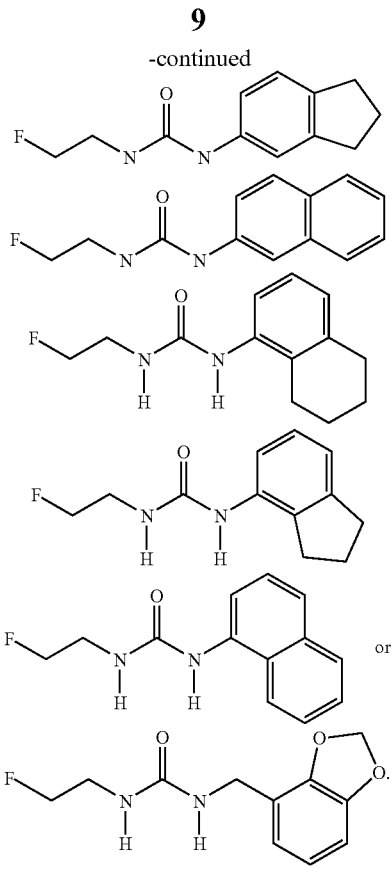

In still other embodiments of the invention, there are provided aryl fluoroethyl ureas according to Formula 1 wherein $R_1$ is alkyl, phenyl, or substituted phenyl. Exemplary compounds according to these embodiments of the invention include, but are not limited to, compounds having the structure:

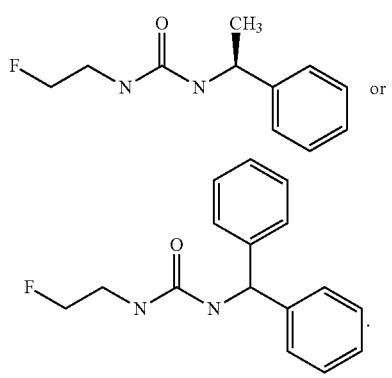

Schemes A-D outline general methods for producing aryl fluoroethyl ureas according to the invention. In Scheme A an exemplary method for producing alkyl-substituted aryl fluoroethyl ureas is set forth. An appropriately substituted alkyl-aryl isocyanate reacts with fluoroethyl amine hydrochloride in a suitable solvent, such as methylene chloride, acetonitrile, or the like. This mixture is stirred at room temperature in the presence of diisopropylethyl amine (DIEA) for about 14 hours. After routine workup procedures, the desired alkyl-substituted aryl fluoroethyl urea is obtained after recrystallization.

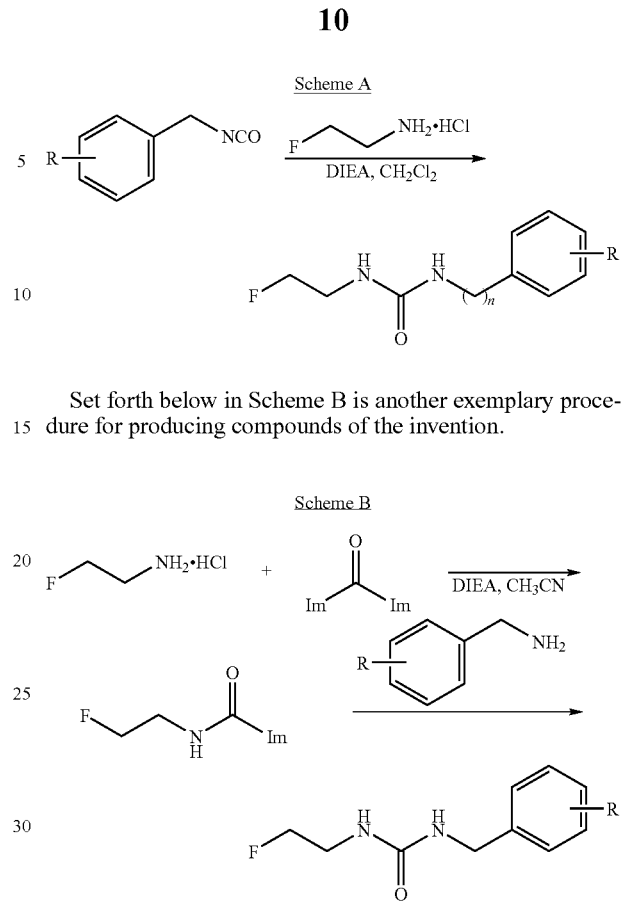

Set forth below in Scheme B is another exemplary procedure for producing compounds of the invention.

As depicted in Scheme B, diimidazole carbonyl (1 eq) and fluoroethylamine hydrochloride (1 eq) react in an appropriate solvent (such as acetonitrile) in the presence of diisopropylethyl amine (2 eq). An appropriately substituted benzylamine is dissolved in a suitable solvent and then added to the original reaction mixture. The resulting mixture is stirred for about 14 hours. After routine workup procedures, the desired substituted-aryl fluoroethyl urea is obtained after recrystallization.

Scheme C outlines yet another procedure for producing the compounds of the invention.

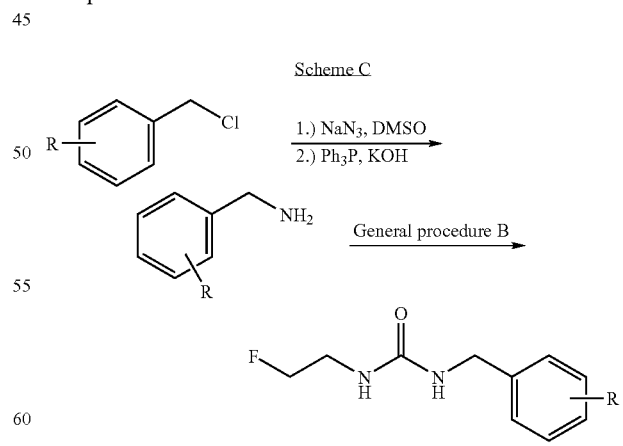

In this procedure, an appropriately substituted benzyl halide and $NaN_3$ are mixed in a solvent such as dimethylformamide (DMF) and stirred at room temperature for about 14 hours. The resulting mixture is diluted with water and extracted with $Et_2O$. The combined organic extracts are washed with H₂O and brine, dried over MgSO₄ and concentrated. The crude azide is dissolved in THF:H₂O (3:1) and Ph₃P (1.0 eq) is added, followed by KOH (1.0 eq). After stirring for 14 hours, the reaction mixture is acidified with concentrated HCl. The resulting solution is washed with Et₂O and the aqueous layer was treated with NH₃ and extracted with Et₂O. The combined organic extracts are washed with H₂O and brine, then dried over MgSO₄ and concentrated to give the desired substituted benzylamine. This amine is then converted to an aryl fluoroethyl urea of the invention via the protocols described in Scheme B.

Scheme D describes still another procedure for producing the compounds of the invention.

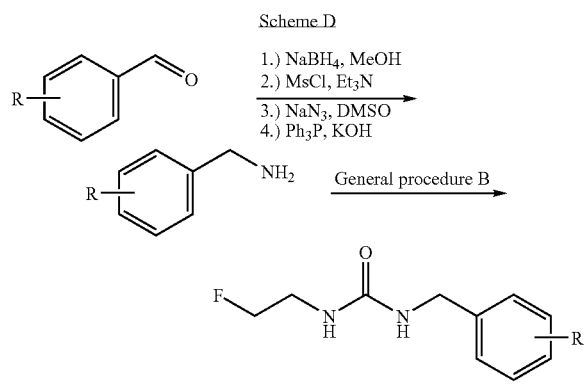

In this procedure, an appropriate benzaldehyde is dissolved in ether and after cooling to 0° C., NaBH₄ (1.0 eq) in methanol is slowly added. The reaction mixture is stirred at this temperature for about 1 hour, then quenched with saturated NH₄Cl and the resulting mixture is extracted with Et₂O. The combined organic extracts are washed with H₂O and brine, then dried over MgSO₄ and concentrated. Column chromatography using hexane:EtOAc (3:2) as the eluant gives the desired benzyl alcohol. The benzylalcohol (1.0 eq) is dissolved in CH₂Cl₂, cooled to 0° C. Next, MsCl (1.5 eq) is added, followed by Et₃N (2.0 eq). The resulting mixture is allowed to warm to room temperature and is stirred for about 14 hours. The reaction mixture is diluted with dichloromethane and washed with H₂O and brine, then dried over MgSO₄ and concentrated. This crude mesylate is converted into the desired amine with NaN₃ (3.0 eq), Ph₃P (1.0 eq) and KOH (1.0 eq) according to the protocols as outlined in Scheme C. The aryl substituted fluoroethyl urea of the invention is thus obtained from this amine using the protocols described in general procedure B.

The aryl fluoroethyl ureas of the invention are agonists of alpha₂ adrenergic receptors. The alpha₂ receptor activity of the compounds of the invention is demonstrated in an assay titled Receptor Selection and Amplification technology (RSAT) assay, which is described in the publication by Messier et. Al, 1995, Pharmacol. Toxicol. 76, pp. 308-311 (incorporated herein by reference) and is also described below. Another reference pertinent to this assay is Conklin et al. (1993) Nature 363:274-6, Receptor Selection and Amplification Technology (RSAT) assay, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as ꓱ-galactosidase, the activity of which can be easily measured in a 96-well format. Receptors that activate the G protein, Gq, elicit this response. Alpha 2 receptors, which normally couple to Gi, activate the RSAT response when coexpressed with a hybrid Gq protein that has a Gi receptor recognition domain, called Gq/i5.

NIH-3T3 cells are plated at a density of 2×10⁶ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 µg), receptor (1-2 µg) and G protein (1-2 µg). 40 µg salmon sperm DNA may also be included in the transfection mixture. Fresh media is added on the following day and 1-2 days later, cells are harvested and frozen in 50 assay aliquots. Cells are thawed and 100 µl added to 100 µl aliquots of various concentrations of drugs in triplicate in 96-well dishes. Incubations continue 72-96 hr at 37° C. After washing with phosphate-buffered saline, ꓱ-galactosidase enzyme activity is determined by adding 200 µl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha₂ₐ, alpha₂ᵦ and alpha₂c receptors.

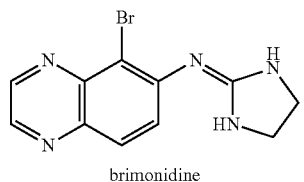 [SMILES: Brc1c(N=C2NCCN2)ccc2nccnc12]

brimonidine

Diseases that may be treated with this invention include, but are not limited to neurodegenerative aspects of the following conditions:
MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration,
UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy
VASCULAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The results of the RSAT assay with several exemplary compounds of the invention are disclosed in Table 1 below together with the chemical structures of these compounds. "Not active" means the compounds are not active at concentrations less than 10 micromolar.

TABLE 1

| Compound | Alpha 2A $EC_{50}$ | Alpha 2A IA | Alpha 2B $EC_{50}$ | Alpha 2B IA | Alpha 2C $EC_{50}$ | Alpha 2C IA |
|---|---|---|---|---|---|---|
| Compound 1 | 1748 | 0.54 | 124 | 1.0 | 1127 | 0.71 |
| Compound 2 | not active | | 152 | 1.13 | 1293 | 0.78 |
| Compound 3 | not active | | 148 | 1.1 | 363 | 0.63 |
| Compound 4 | not active | | 221 | 1.14 | 368 | 0.47 |
| Compound 5 | 980 | 0.48 | 88 | 1.26 | 876 | 0.74 |

TABLE 1-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 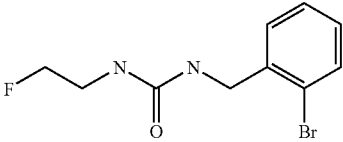<br>Compound 6 | 122 | 0.36 | 85 | 0.9 | 488 | 1.1 |
| 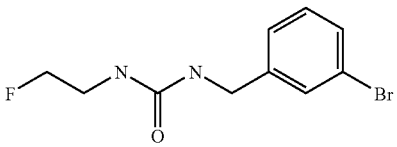<br>Compound 7 | >2000 | 0.46 | 355 | 0.84 | 556 | 0.81 |
| 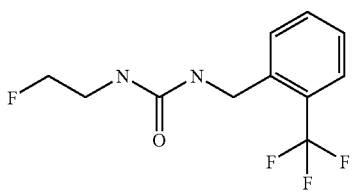<br>Compound 8 | not active | | 569 | 0.8 | 950 | 0.93 |
| 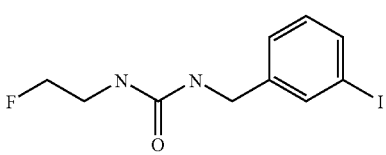<br>Compound 9 | 1482 | 0.48 | 171 | 0.76 | 302 | 0.62 |
| 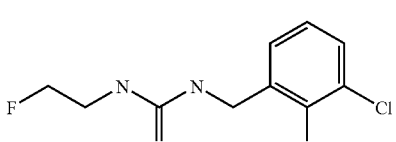<br>Compound 10 | not active | | 88 | 0.91 | 446 | 0.86 |
| 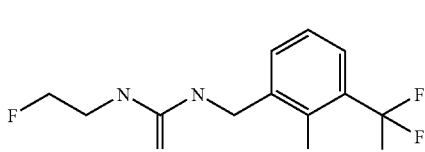<br>Compound 11 | not active | | 106 | 0.9 | 1087 | 0.66 |
| 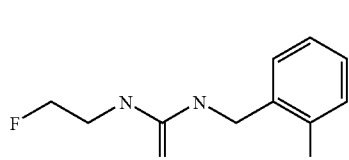<br>Compound 12 | not active | | 277 | 0.89 | 489 | 0.78 |

TABLE 1-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 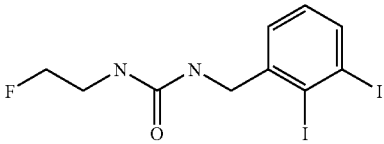 Compound 13 | 1007 | 0.59 | 96 | 0.86 | 192 | 0.72 |
| 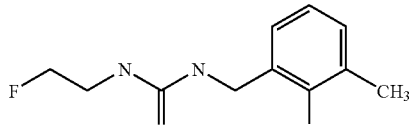 Compound 14 | 366 | 0.34 | 8.5 | 0.85 | 101 | 0.66 |
| 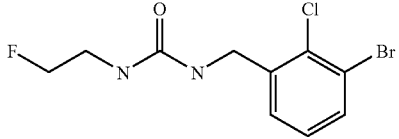 Compound 15 | 224 | 0.46 | 25 | 1.3 | 297 | 0.88 |
| 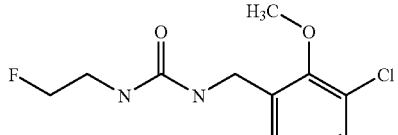 Compound 16 | 1015 | 0.66 | 93 | 1.32 | 724 | 0.72 |
| 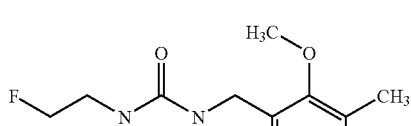 Compound 17 | 678 | 0.79 | 40 | 1.25 | 685 | 0.93 |
| 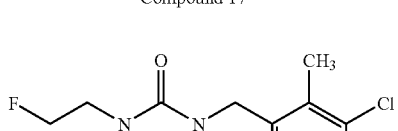 Compound 18 | 400 | 0.36 | 40 | 1.24 | 1385 | 0.94 |
| 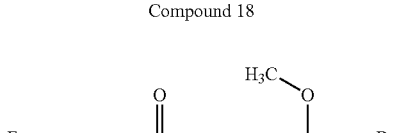 Compound 19 | not active | | 2531 | 0.83 | not active | |

TABLE 1-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 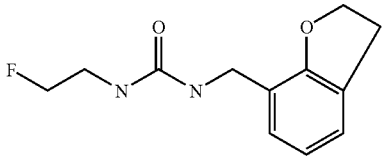 Compound 20 | 147 | 0.51 | 27 | 1.14 | 82 | 0.83 |
| 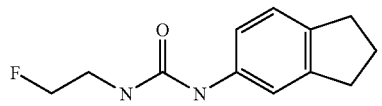 Compound 21 | not active | | 115 | 0.33 | not active | |
| 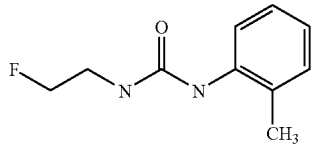 Compound 22 | >2000 | 0.38 | 1535 | 0.92 | >2000 | 0.48 |
| 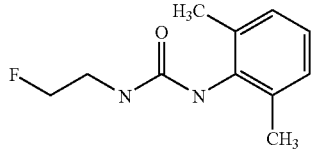 Compound 23 | >2000 | 0.61 | 679 | 0.75 | >2000 | 0.43 |
| 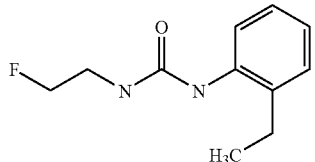 Compound 24 | 2672 | 0.35 | >2000 | 0.82 | >2000 | 0.36 |
| 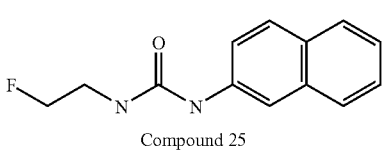 [SMILES: O=C(NCCF)Nc1ccc2ccccc2c1] Compound 25 | 1273 | 0.58 | 1580 | 0.99 | >2000 | 0.59 |
| 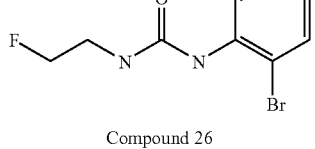 Compound 26 | not active | | 2650 | 0.33 | not active | |
| 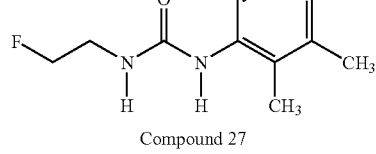 Compound 27 | >2000 | 0.54 | 401 | 0.9 | 740 | 0.73 |

TABLE 1-continued
|  | Alpha 2A | | Alpha 2B | | Alpha 2C | |
|---|---|---|---|---|---|---|
|  | EC$_{50}$ | IA | EC$_{50}$ | IA | EC$_{50}$ | IA |
| 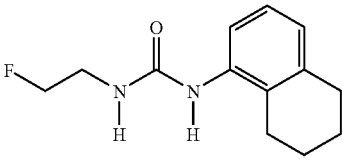<br>Compound 28 | 385 | 0.43 | 157 | 0.87 | 285 | 0.74 |
| 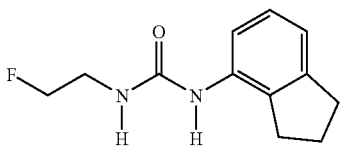<br>Compound 29 | 940 | 0.37 | 1221 | 0.89 | 2550 | 0.63 |
| 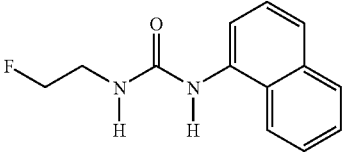<br>Compound 30 | 1063 | 0.74 | 458 | 0.9 | >2000 | 0.66 |
| 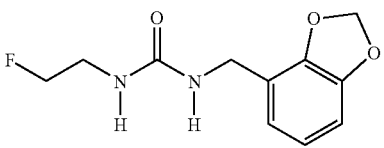<br>Compound 31 | >2000 | 0.48 | 119 | 1.0 | 2017 | 1.2 |
| 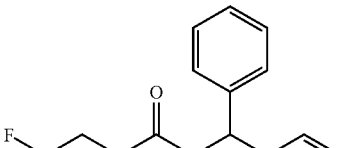<br>Compound 32 | not active | | 325 | 0.58 | not active | |
| 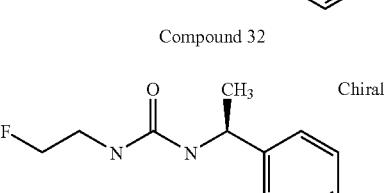 Chiral<br>Compound 33 | 302 | 0.63 | 66 | 0.99 | 513 | 0.64 |
| 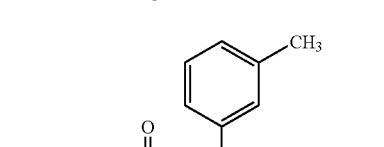<br>Compound 34 | not active | | 829 | 0.41 | not active | |

TABLE 1-continued
| | Alpha 2A | | Alpha 2B | | Alpha 2C | |
|---|---|---|---|---|---|---|
| | $EC_{50}$ | IA | $EC_{50}$ | IA | $EC_{50}$ | IA |
| 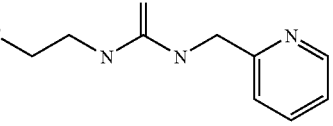 Compound 35 | not active | | 1992 | 0.75 | 3707 | 0.38 |
| 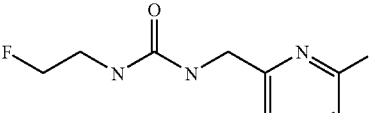 Compound 36 | 1757 | 0.62 | 414 | 0.78 | 1796 | 0.52 |
| 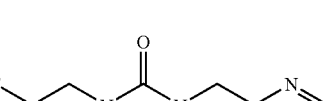 Compound 37 | not active | | 3537 | 0.40 | not active | |
| 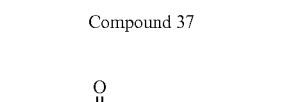 Compound 38 | not active | | 592 | 0.85 | 2164 | 0.65 |
| 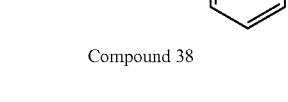 Compound 39 | 2173 | 0.36 | 343 | 0.77 | 1556 | 0.61 |
| 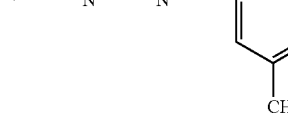 Compound 40 | not active | | 968 | 0.83 | 2626 | 0.56 |
| 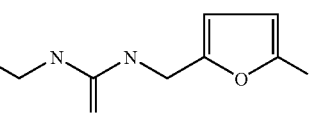 Compound 41 | not active | | 293 | 0.84 | 800 | 0.69 |

TABLE 1-continued

| | Alpha 2A | | Alpha 2B | | Alpha 2C | |
|---|---|---|---|---|---|---|
| | EC$_{50}$ | IA | EC$_{50}$ | IA | EC$_{50}$ | IA |
| Compound 42 | 3516 | 0.33 | 137 | 0.81 | 1057 | 0.67 |
| Compound 43 | 4204 | 0.30 | 2386 | 0.49 | not active | |
| Compound 44 | not active | | 2280 | 0.67 | 4158 | 0.31 |

Generally speaking, alpha$_2$ agonists can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha$_2$ agonists including alpha$_{2B/2C}$ agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of alpha$_{2B}$ and/or alpha$_{2C}$ adrenergic receptors in preference over alpha$_{2A}$ receptors, if the compound is more active, preferably at least ten (10) times more active towards either alpha$_{2B}$ or towards alpha$_{2C}$ receptors than towards alpha$_{2A}$ receptors. It can be seen from these tables that several compounds of the invention are specific or selective agonists of alpha$_{2B}$ and/or alpha$_{2C}$ adrenergic receptors within the former definition, and have no agonist like activity or only insignificant agonist-like activity on alpha$_{2A}$ receptors. However, compounds of the invention which are active as agonists of all three alpha$_2$ receptors (pan agonists) are also desirable.

Thus, the aryl fluoroethyl ureas of the invention are useful for treating conditions and diseases which are responsive to treatment by alpha 2 and particularly by alpha$_{2B}$ and/or alpha$_{2C}$ adrenergic receptor agonists. Such conditions and diseases include, but are not limited to, pain including chronic pain (which may be, without limitation visceral, inflammatory, referred or neuropathic in origin), neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis.

The activity of the compounds of the invention is highly advantageous because the administration of these compounds to mammals does not result in sedation or in significant cardiovascular effects (such as changes in blood pressure or heart rate).

The compounds of the invention act and can be used as a highly effective analgesic, particularly in chronic pain models, with minimal undesirable side effects, such as sedation and cardiovascular depression, commonly seen with other agonists of the alpha$_2$ receptors.

Invention aryl fluoroethyl ureas may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

Invention compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of Formula 1 in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the invention can be used in the form of a solid, a solution, an emulsion, a dispersion, a micelle, a liposome, and the like, wherein the resulting composition contains one or more aryl fluoroethyl ureas of the present invention, as an active ingredient, in admixture with an organic or inorganic carrier or excipient suitable for enteral or parenteral applications. Invention aryl fluoroethyl ureas may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention aryl fluoroethyl ureas are included in the pharmaceutical composition in an amount sufficient to produce the desired effect upon the process or disease condition.

Pharmaceutical compositions containing invention aryl fluoroethyl ureas may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention aryl fluoroethyl ureas in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention aryl fluoroethyl ureas may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists of alpha$_2$ adrenergic receptors. The compositions containing the compounds of the invention are primarily, but not exclusively, used for alleviation of chronic pain and/or allodynia. Some of the compounds of the invention have the demonstrable advantageous property that they are specific or selective to alpha$_{2B}$ and/or alpha$_{2C}$ adrenergic receptors in preference over alpha$_{2A}$ adrenergic receptors. In addition, some of the alpha$_2$ agonist compounds have no or only minimal cardiovascular and/or sedatory activity.

Thus, in further embodiments of the invention, there are provided methods for treating a disorder associated with modulation of alpha$_2$ adrenergic receptors. Such methods can be performed, for example, by administering to a subject in need thereof a pharmaceutical composition containing a therapeutically effective amount of at least one invention compound of Formula 1. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

Typical disorders that can be treated by the compounds and pharmaceutical compositions described herein include, but are not limited to, chronic pain, visceral pain, neuropathic pain, corneal pain, glaucoma, elevated intraocular pressure, ischemic neuropathies, neurodegenerative diseases, diarrhea, nasal congestion, muscle spasticity, diuresis, withdrawal syndromes, neurodegenerative diseases, optic neuropathy, spinal ischemia, stroke, memory and cognition deficits, attention deficit disorder, psychoses, manic disorders, anxiety, depression, hypertension, congestive heart failure, cardiac ischemia, arthritis, spondylitis, gouty arthritis, osteoarthritis, juvenile arthritis, autoimmune diseases, lupus erythematosus, chronic gastrointestinal inflammations, Crohn's disease, gastritis, irritable bowel syndrome (IBS), functional dyspepsia, ulcerative colitis, allodynia, or a combination thereof.

In one embodiment, the disorder is chronic pain.
In one embodiment, the disorder is visceral pain.
In one embodiment, the disorder is neuropathic pain.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A∃ and A* fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A∃ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

In still another embodiment of the invention, there are provided methods for treating a disorder associated with modulation of alpha2 adrenergic receptors. Such methods can be performed, for example, by administering to a subject in need thereof a therapeutically effective amount of at least one compound of Formula 1, or any combination thereof, or pharmaceutically acceptable salts, hydrates, solvates, crystal forms and individual isomers, enantiomers, and diastereomers thereof.

The following examples are intended only to illustrate the present invention and should in no way be construed as limiting the subject invention.

EXAMPLES

General Considerations

Proton nuclear magnetic resonance ($^1$H NMR) and carbon nuclear magnetic resonance ($^{13}$C NMR) spectra were recorded on a Varian 300 or 500 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

General Procedure A for the Synthesis of Fluoroethyl Alkyl Aryl Ureas:

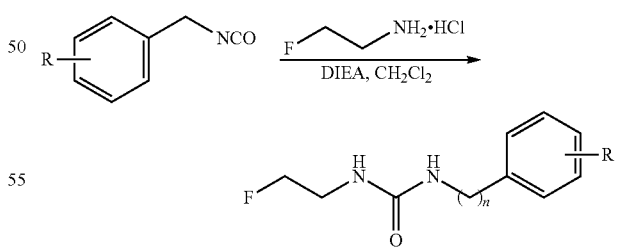

Alkyl aryl isocyanate (1.0 eq) and fluoroethyl amine hydrochloride (1.0 eq) were mixed in CH$_2$Cl$_2$ or CH$_3$CN. The resulting mixture was stirred for a few minutes, diisopropylethyl amine (2.0 eq) was added and the reaction mixture was stirred for 14 hours. The reaction mixture was diluted with EtOAc and washed with H$_2$O (5×30 mL). Concentration gave the crude product. The pure final product was obtained after recrystallization in CH$_3$CN.

Example 1

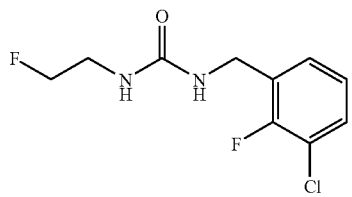 [SMILES: O=C(NCCF)NCc1cccc(Cl)c1F]

Synthesis of 1-(3-chloro-2-fluoro-benzyl)-3-(2-fluoro-ethyl)-urea (Compound 1)

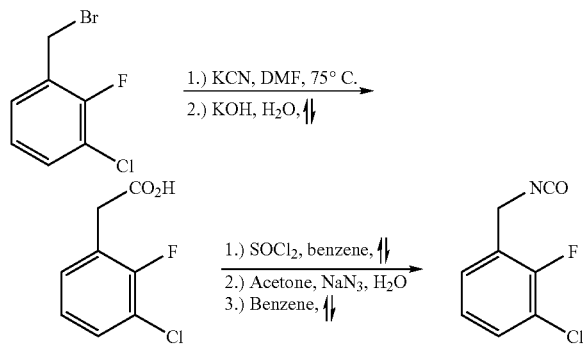

(3-Chloro-2-fluoro-phenyl)-acetic acid: 1-Bromomethyl-3-chloro-2-fluoro-benzene (10.00 g, 44.80 mmol) and KCN (5.80 g, 89.07 mmol) were mixed in DMF and the resulting reaction mixture was stirred at 75° C. for 2 days. The reaction mixture was cooled to room temperature, and water was added. The mixture was extracted with $Et_2O$ (3×300 mL). The combined organic phases were washed with $H_2O$ (2×200 mL) and brine (1×200 mL), then dried over $MgSO_4$ and concentrated. The crude nitrile was taken up in water and KOH (5.00 g, 89.11 mmol) was added. The resulting mixture was refluxed for 14 hours. After cooling to room temperature, the reaction mixture was diluted with water and washed with $Et_2O$ (2×150 mL). The aqueous layer was acidified with concentrated HCl and was extracted with $Et_2O$ (3×300 mL). The combined organic phases were washed with $H_2O$ (2×200 mL) and brine (1×200 mL), then dried over $MgSO_4$ and concentrated to afford the title acid.

1-Chloro-2-fluoro-3-isocyanatomethyl-benzene: A solution of (3-chloro-2-fluoro-phenyl)-acetic acid (crude, taken from the previous step) and $SOCl_2$ (6.50 mL, 89.11 mmol) in benzene was refluxed for 3 hours. After cooling to room temperature, the reaction mixture was concentrated on a rotary evaporator. The residue was dissolved in acetone and $NaN_3$ (5.80 g, 89.22 mmol) dissolved in minimum amount of $H_2O$ was added. The resulting solution was stirred at room temperature for 3 hours. The reaction mixture was then diluted with benzene and washed with $H_2O$ (1×50 mL) and brine (1×50 mL), then dried over $MgSO_4$ and concentrated. The residue was dissolved in benzene and was refluxed for 30 minutes. Evaporation of the solvent gave the desired isocyanate.

1-(3-Chloro-2-fluoro-benzyl)-3-(2-fluoro-ethyl)-urea: The title compound was obtained from 1-chloro-2-fluoro-3-isocyanatomethyl-benzene (5.00 g, 27.00 mmol), fluoroethyl amine hydrochloride (4.00 g, 90% purity, 36.18 mmol) and diisopropylethyl amine (9.50 mL, 54.54 mmol) according to the protocols as outlined in general procedure A above. Spectroscopic data: $^{13}C$ NMR (75 MHz, DMSO-$d_6$) δ 37.7, 40.5 (d, J=21.9 Hz), 84.0 (d, J=163.5 Hz), 120.1 (d, J=18.4 Hz), 125.8, 128.7, 129.5, 130.4 (d, J=15.0 Hz), 154.1 (d, J=247.5 Hz), 158.5.

Example 2

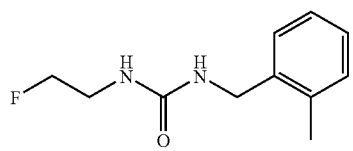

Synthesis of 1-(2-fluoro-ethyl)-3-(2-methyl-benzyl)-urea (Compound 2)

1-(2-Fluoro-ethyl)-3-(2-methyl-benzyl)-urea: The title urea was obtained from isocyanatomethyl-2-methyl-benzene (5.00 g, 34.00 mmol), fluoroethyl amine hydrochloride (5.00 g, 90% purity, 45.23 mmol) and diisopropylethyl amine (12.00 mL, 68.90 mmol) according to the protocols as outlined in general procedure A. Spectroscopic data: $^1H$ NMR (300 MHz, DMSO-$d_6$) δ 2.3 (s, 3H), 3.3 (s, 2H), 4.2 (d, J=5.9 Hz, 2H), 4.3 (t, J=5.0 Hz, 1H), 4.5 (t, J=5.0 Hz, 1H), 6.2 (t, J=5.3 Hz, 1H), 6.3 (t, J=5.6 Hz, 1H), 7.09-7.23 (m, 4H). $^{13}C$ NMR (75 MHz, DMSO-$d_6$) δ 19.1, 40.6 (d, J=20.7 Hz), 41.7, 84.1 (d, J=164.1 Hz), 126.4, 127.3, 127.9, 130.5, 136.1, 138.9, 158.6.

Example 3

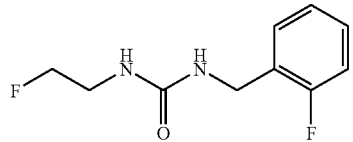 [SMILES: O=C(NCCF)NCc1ccccc1F]

Synthesis of 1-(2-fluoro-benzyl)-3-(2-fluoro-ethyl)-urea (Compound 3)

1-(2-Fluoro-benzyl)-3-(2-fluoro-ethyl)-urea: The title compound was obtained from 1-fluoro-2-isocyanatomethyl-benzene (5.00 g, 33. mmol), fluoroethyl amine hydrochloride (5.00 g, 90% purity, 45.23 mmol) and diisopropylethyl amine (11.50 mL, 66.02 mmol) according to the protocols as outlined in general procedure A above. Spectroscopic data: $^1H$ NMR (300 MHz, DMSO-$d_6$) δ 3.21-3.42 (m, 2H), 4.25 (d, J=5.9 Hz, 2H), 4.32 (t, J=5.3 Hz, 1H), 4.5 (t, J=5.0 Hz, 1H), 6.2 (t, J=5.3 Hz, 1H), 6.5 (t, J=5.6 Hz, 1H), 7.11-7.21 (m, 2H), 7.25-7.35 (m, 2H). $^{13}C$ NMR (75 MHz, DMSO-$d_6$) δ 37.4 (d, J=4.6 Hz), 40.6 (d, J=20.7 Hz), 84.0 (d, J=164.1 Hz), 115.6

(d, J=20.7 Hz), 124.8 (d, J=3.4 Hz), 128.0 (d, J=13.8 Hz), 129.2 (d, J=8.0 Hz), 129.9 (d, J=4.6 Hz), 158.6, 160.7 (d, J=244.4 Hz).

Example 4

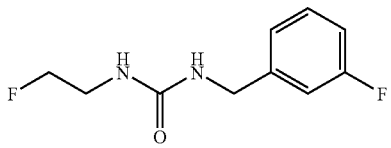 [SMILES: O=C(NCCF)NCc1cccc(F)c1]

Synthesis of 1-(3-fluoro-benzyl)-3-(2-fluoro-ethyl)-urea (Compound 4)

1-(3-Fluoro-benzyl)-3-(2-fluoro-ethyl)-urea: The title compound was obtained from 1-fluoro-3-isocyanatomethyl-benzene (5.00 g, 33.00 mmol), fluoroethyl amine hydrochloride (5.00 g, 90% purity, 45.23 mmol) and diisopropylethyl amine (11.50 mL, 66.02 mmol) according to the protocols as outlined in general procedure A above. Spectroscopic data: $^1$H NMR (300 MHz, DMSO-$d_6$) δ 3.25-3.41 (m, 2H), 4.23 (d, J=5.9 Hz, 2H), 4.47 (t, J=5.0 Hz, 1H), 4.5 (t, J=5.0 Hz, 1H), 6.3 (s, 1H), 6.5 (s, 1H), 6.99-7.14 (m, 3H), 7.28-7.42 (m, 1H). $^{13}$C NMR (75 MHz, DMSO-$d_6$) δ 40.6 (d, J=20.7 Hz), 43.1, 83.9 (d, J=165.2 Hz), 113.8 (t, J=21.8 Hz, 2C), 123.4, 130.3 (d, J=8.0 Hz), 144.6 (d, J=6.9 Hz), 158.8, 163.0 (d, J=243.2 Hz).

Example 5

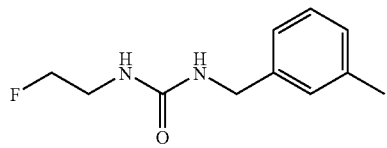

Synthesis of 1-(2-fluoro-ethyl)-3-(3-methyl-benzyl)-urea (Compound 5)

1-(2-Fluoro-ethyl)-3-(3-methyl-benzyl)-urea: The title compound was obtained from 1-isocyanatomethyl-3-methyl-benzene (1.47 g, 8.80 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-$d_6$) δ 2.3 (s, 3H), 3.24-3.39 (m, 2H), 4.2 (d, J=6.2 Hz, 2H), 4.3 (t, J=5.0 Hz, 1H), 4.5 (t, J=5.0 Hz, 1H), 6.2 (t, J=5.6 Hz, 1H), 6.4 (t, J=5.9 Hz, 1H), 7.00-7.07 (m, 3H), 7.2 (t, J=7.9, 7.3 Hz, 1H). $^{13}$C NMR (75 MHz, DMSO-$d_6$) δ 21.6, 40.6 (d, J=20.7 Hz), 43.6, 84.0 (d, J=165.2 Hz), 124.8, 127.9, 128.3, 128.8, 137.9, 141.3, 158.7.

General Procedure B for the Synthesis of Fluoroethyl Substituted Benzyl Ureas

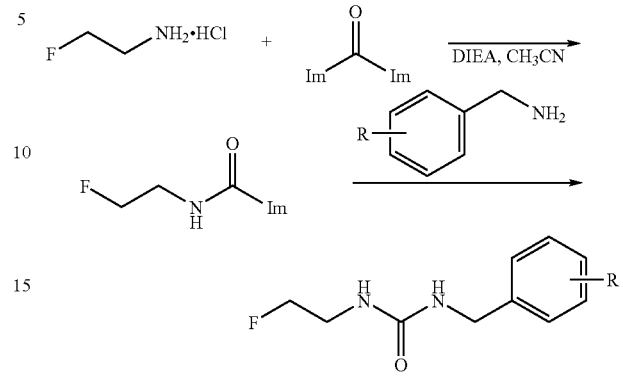

A solution of diimidazole carbonyl (1 eq) and fluoroethylamine hydrochloride (1 eq) in acetonitrile in the presence of diisopropylethyl amine (2 eq) was stirred for 45 minutes. An appropriately substituted benzylamine in acetonitrile was then added and the resulting mixture was stirred for 14 hours. The reaction mixture was diluted with EtOAc and washed with H$_2$O (3×75 mL) and brine (1×50 mL), then dried over MgSO$_4$ and concentrated. The crude product was purified by recrystallization in CH$_3$CN to afford the final pure product.

Example 6

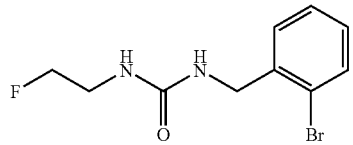 [SMILES: O=C(NCCF)NCc1ccccc1Br]

Synthesis of 1-(2-bromo-benzyl)-3-(2-fluoro-ethyl)-urea (Compound 6)

1-(2-Bromo-benzyl)-3-(2-fluoro-ethyl)-urea: The title compound was obtained from 2-bromo-benzylamine (1.90 g, 10.20 mmol), diimidazole carbonyl (1.70 g, 10.48 mmol), fluoroethylamine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.24-3.39 (m, 2H), 4.2 (d, J=6.2 Hz, 2H), 4.3 (t, J=5.0 Hz, 1H), 4.5 (t, J=5.3 Hz, 1H), 6.4 (t, J=5.6 Hz, 1H), 6.5 (t, J=6.2 Hz, 1H), 7.16-7.23 (m, 1H), 7.28-7.40 (m, 2H), 7.56-7.61 (m, 1H). $^{13}$C NMR (75 MHz, DMSO-$d_6$) δ 40.6 (d, J=20.7 Hz), 44.0, 84.0 (d, J=164.1 Hz), 122.9, 128.3, 129.3 (2C), 132.9, 139.9, 158.5.

Example 7

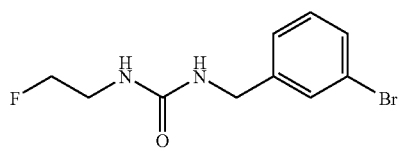 [SMILES: O=C(NCCF)NCc1cccc(Br)c1]

Synthesis of 1-(3-bromo-benzyl)-3-(2-fluoro-ethyl)-urea (Compound 7)

1-(3-Bromo-benzyl)-3-(2-fluoro-ethyl)-urea: The title compound was obtained from 3-bromo-benzylamine (1.90 g, 10.20 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.24-3.39 (m, 2H), 4.2 (d, J=6.2 Hz, 2H), 4.3 (t, J=5.0 Hz, 1H), 4.5 (t, J=5.3 Hz, 1H), 6.3 (t, J=5.9 Hz, 1H), 6.5 (t, J=5.9 Hz, 1H), 7.22-7.31 (m, 2H), 7.38-7.46 (m, 2H). $^{13}$C NMR (75 MHz, DMSO-$d_6$) δ 40.6 (d, J=20.7 Hz), 43.0, 84.0 (d, J=164.1 Hz), 122.3, 126.7, 130.0, 130.3, 131.0, 144.5, 158.6.

Example 8

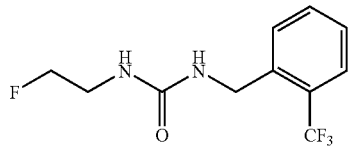 [SMILES: O=C(NCCF)NCc1ccccc1C(F)(F)F]

Synthesis of 1-(2-fluoro-ethyl)-3-(2-trifluoromethyl-benzyl)-urea (Compound 8)

1-(2-Fluoro-ethyl)-3-(2-trifluoromethyl-benzyl)-urea: The title compound was obtained from 2-trifluoromethyl-benzylamine (1.80 g, 10.30 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.25-3.40 (m, 2H), 4.3 (t, J=5.0 Hz, 1H), 4.4 (d, J=5.9 Hz, 2H), 4.5 (t, J=5.0 Hz, 1H), 6.4 (t, J=5.6 Hz, 1H), 6.5 (t, J=6.2, 5.6 Hz, 1H), 7.41-7.55 (m, 2H), 7.61-7.72 (m, 2H). $^{13}$C NMR (75 MHz, DMSO-$d_6$) δ 40.6 (d, J=20.7 Hz), 84.0 (d, J=164.1 Hz), 125.2 (d, J=274.2 Hz), 126.1 (d, J=5.7 Hz), 126.3 (d, J=5.7 Hz), 126.7 (d, J=29.8 Hz), 127.7, 129.3, 133.2, 139.9, 158.5.

Example 9

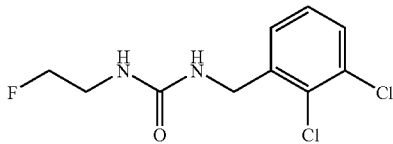 [SMILES: O=C(NCCF)NCc1cccc(Cl)c1Cl]

Synthesis of 1-(2,3-dichloro-benzyl)-3-(2-fluoro-ethyl)-urea (Compound 10)

1-(2,3-Dichloro-benzyl)-3-(2-fluoro-ethyl)-urea: A solution of 2,3-dichloro-benzylamine (1.80 g, 10.20 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.24-3.39 (m, 2H), 4.27-4.35 (m, 3H), 4.5 (t, J=5.3, 4.7 Hz, 1H), 6.4 (t, J=5.6 Hz, 1H), 6.6 (t, J=6.2 Hz, 1H), 7.28 (dd, J=7.6 Hz, 1H), 7.33 (t, J=7.6 Hz, 1H), 7.5 (dd, J=7.9 Hz, 1H). $^{13}$C NMR (75 MHz, DMSO-$d_6$) δ 40.6 (d, J=21.8 Hz), 42.2, 84.0 (d, J=164.1 Hz) 127.6, 128.6, 129.3, 130.4, 132.2, 141.3, 158.4.

Example 10

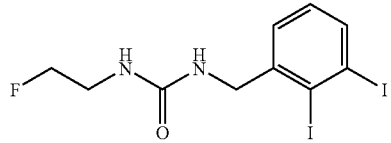 [SMILES: O=C(NCCF)NCc1cccc(I)c1I]

Synthesis of 1-(2-fluoro-ethyl)-3-(2,3-diiodo-benzyl)-urea (Compound 13)

1-(2-Fluoro-ethyl)-3-(2,3-diiodo-benzyl)-urea: The title compound was obtained from 2,3-diiodo-benzylamine (3.60 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.23-3.38 (m, 2H), 4.25 (d, J=5.9 Hz, 2H), 4.3 (t, J=5.3 Hz, 1H), 4.5 (t, J=5.0 Hz, 1H), 6.2 (t, J=6.2 Hz, 1H), 6.5 (t, J=5.6 Hz, 1H), 7.10-7.20 (m, 1H), 7.25-7.34 (m, 2H).

Example 11

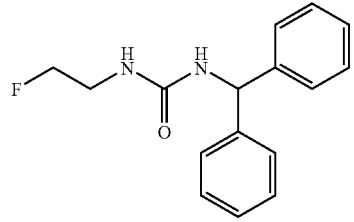 [SMILES: O=C(NCCF)NC(c1ccccc1)c1ccccc1]

Synthesis of 1-benzhydryl-3-(2-fluoro-ethyl)-urea (Compound 32)

1-Benzhydryl-3-(2-fluoro-ethyl)-urea: The title compound was obtained from diphenyl-methylamine (1.84 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.23-3.39 (m, 3H), 4.26-4.37 (m, 1H), 4.40-4.51 (m, 1H), 5.9 (d, J=8.2 Hz, 1H), 6.11-6.26 (m, 1H), 6.98-7.10 (m, 2H), 7.20-7.35 (m, 8H).

Example 12

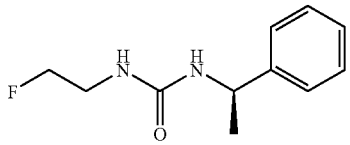

Synthesis of (−)-(S)-1-(2-Fluoro-ethyl)-3-(1-phenyl-ethyl)-urea (Compound 33)

(−)-(S)-1-(2-Fluoro-ethyl)-3-(1-phenyl-ethyl)-urea: The title compound was obtained from (S)-1-phenyl-ethylamine (1.20 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 1.3 (d, J=6.7 Hz, 3H), 3.20-3.27 (m, 1H), 3.29-3.37 (m, 1H), 4.3 (t, J=5.0 Hz, 1H), 4.5 (t, J=5.0 Hz, 1H), 4.68-4.81 (m, 1H), 6.0 (t, J=5.3 Hz, 1H), 6.5 (d, J=7.9 Hz, 1H), 7.19-7.35 (m, 5H).

General Procedure C for the Synthesis of Fluoroethyl Substituted Benzyl Ureas

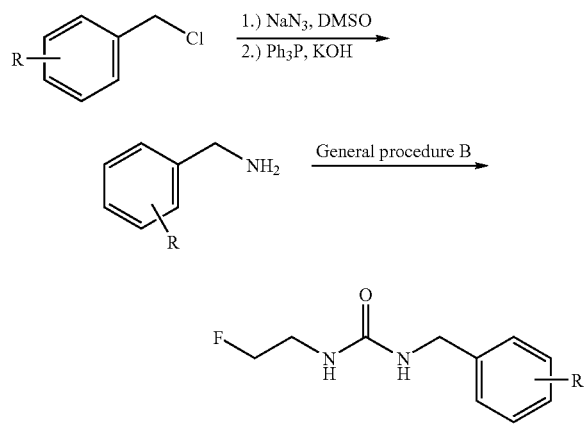

An appropriately substituted benzyl halide (79.40 mmol) and NaN$_3$ (2.0 eq) were mixed in DMF and was stirred at room temperature for 14 hours. The resulting mixture was diluted with water and extracted with Et$_2$O (3×300 mL). The combined organic extracts were washed with H$_2$O (3×150 mL) and brine (1×150 mL), then dried over MgSO$_4$ and concentrated. The crude azide was dissolved in THF:H$_2$O (3:1) and Ph$_3$P (1.0 eq) was added, followed by KOH (1.0 eq). The reaction mixture was stirred for 14 hours, and then was acidified with concentrated HCl. The resulting solution was washed with Et$_2$O and the aqueous layer was basified with NH$_3$ and extracted with Et$_2$O (3×200 mL). The combined organic extracts were washed with H$_2$O (3×100 mL) and brine (1×100 mL), then dried over MgSO$_4$ and concentrated to give the desired substituted benzylamine. This amine was thus converted to the desired title urea via the protocols described in general procedure B.

Example 13

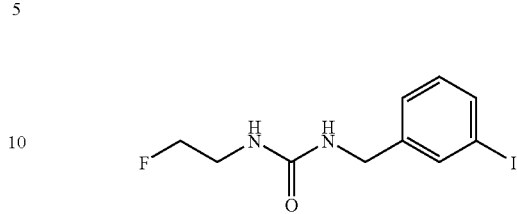

Synthesis of 1-(2-fluoro-ethyl)-3-(3-iodo-benzyl)-urea (Compound 9)

3-Iodo-benzylamine: The title amine was obtained from 3-iodobenzylchloride (20.00 g, 79.4 mmol), NaN$_3$ (10.30 g, 0.16 mol), Ph$_3$P (21.00 g, 80.07 mmol) and KOH (4.50 g, 80.20 mmol) according to the protocols described in general procedure C.

1-(2-Fluoro-ethyl)-3-(3-iodo-benzyl)-urea: The title compound was obtained from 3-iodo-benzylamine (2.40 g, 10.30 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.24-3.38 (m, 2H), 4.2 (d, J=6.2 Hz, 2H), 4.3 (t, J=5.0 Hz, 1H), 4.5 (t, J=5.0 Hz, 1H), 6.2 (t, J=5.9 Hz, 1H), 6.5 (t, J=6.2 Hz, 1H), 7.1 (t, J=7.6 Hz, 1H), 7.3 (d, J=7.6 Hz, 1H), 7.56-7.63 (m, 2H). $^{13}$C NMR (75 MHz, DMSO-$d_6$) δ 40.6 (d, J=21 Hz), 42.9, 84.0 (d, J=164.1 Hz), 95.4, 127.1, 131.1, 135.9, 136.2, 144.4, 158.6.

Example 14

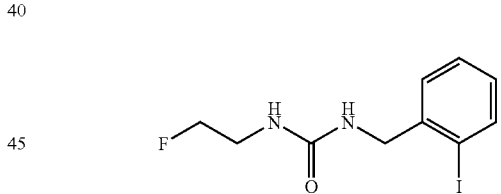

Synthesis of 1-(2-fluoro-ethyl)-3-(2-iodo-benzyl)-urea (Compound 12)

2-Iodo-benzylamine: The title amine was obtained from 2-iodobenzylchloride (20.0 g, 79.40 mmol), NaN$_3$ (10.30 g, 0.16 mol), Ph$_3$P (21.00 g, 80.06 mmol) and KOH (4.50 g, 80.20 mmol) according to the protocols described in general procedure C.

1-(2-Fluoro-ethyl)-3-(2-iodo-benzyl)-urea: The title compound was obtained from 2-iodo-benzylamine (2.40 g, 10.30 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.25-3.39 (m, 2H), 4.2 (d, J=5.9 Hz, 2H), 4.3 (t, J=5.0 Hz, 1H), 4.5 (t, J=5.0 Hz, 1H), 6.4 (t, J=6.2, 5.3 Hz, 1H), 6.5 (t, J=6.2 Hz, 1H), 7.0 (t, J=7.3 Hz, 1H), 7.3 (d, J=7.6 Hz, 1H), 7.4 (t, J=7.6

Hz, 1H), 7.8 (d, J=7.6 Hz, 1H). $^{13}$C NMR (75 MHz, DMSO-d$_6$) δ 40.6 (d, J=20.7 Hz), 48.9, 84.0 (d, J=165.2 Hz), 99.2, 128.7, 128.9, 129.5, 139.5, 142.7, 158.5.

General Procedure D for the Synthesis of Fluoroethyl Substituted Benzyl Ureas:

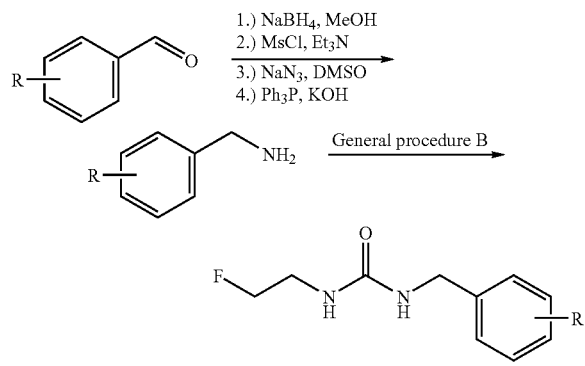

An appropriate benzaldehyde (48.00 mmol) was dissolved in ether and then cooled to 0° C., NaBH$_4$ (1.0 eq) in methanol was slowly added. The reaction mixture was stirred at this temperature for 1 hour, then quenched with saturated NH$_4$Cl and the resulting mixture was extracted with Et$_2$O (3×250 mL). The combined organic extracts were washed with H$_2$O (3×150 mL) and brine (1×150 mL), then dried over MgSO$_4$ and concentrated. Column chromatography using hexane: EtOAc (3:2) as the eluant gave the desired benzyl alcohol. This benzylalcohol (1.0 eq) was dissolved in CH$_2$Cl$_2$, cooled to 0° C., MsCl (1.5 eq) was added, followed by Et$_3$N (2.0 eq). The resulting mixture was allowed to warm to room temperature and stirred for 14 hours. The reaction mixture was diluted with dichloromethane and washed with H$_2$O (3×100 mL) and brine (1×150 mL), then dried over MgSO$_4$ and concentrated. This crude mesylate was converted into the desired title amine with NaN$_3$ (3.0 eq), Ph$_3$P (1.0 eq) and KOH (1.0 eq) according to the protocols as outlined in general procedure C. The final urea was thus obtained from this amine using the protocols described in general procedure B.

Example 15

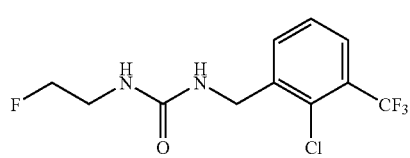 [SMILES: O=C(NCCF)NCc1cccc(C(F)(F)F)c1Cl]

Synthesis of 1-(2-chloro-3-trifluoromethyl-benzyl)-3-(2-fluoro-ethyl)-urea (Compound 11)

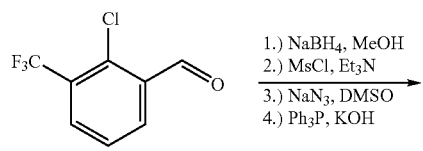

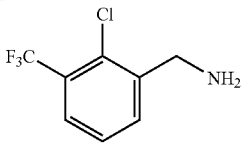

2-Chloro-3-trifluoromethyl-benzylalcohol: The title alcohol was obtained from 2-chloro-3-trifluoromethyl-benzaldehyde (10.00 g, 48.00 mmol) was dissolved in ether and then cooled to 0° C., NaBH$_4$ (1.80 g, 47.58 mmol) according to the protocols described in general procedure D.

2-Chloro-3-trifluoromethyl-benzylamine: The title amine was obtained from 2-chloro-3-trifluoromethyl-benzylalcohol (9.80 g, 46.70 mmol), MsCl (5.40 ml, 69.77 mmol), Et$_3$N (13.00 mL, 93.27 mmol), NaN$_3$ (6.00 g, 92.29 mmol), Ph$_3$P (12.20 g, 46.51 mmol) and KOH (2.60 g, 46.34 mmol) according to the protocols as outlined in general procedure D.

1-(2-Chloro-3-trifluoromethyl-benzyl)-3-(2-fluoro-ethyl)-urea: The title compound was obtained from 2-chloro-3-trifluoromethyl-benzylamine (2.10 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-d$_6$) δ 3.24-3.39 (m, 2H), 4.28-4.39 (m, 3H), 4.5 (t, J=5.0 Hz, 1H), 6.4 (t, J=6.2, 5.3 Hz, 1H), 6.6 (t, J=5.9 Hz, 1H), 7.58 (t, J=7.6 Hz, 1H), 7.63 (d, J=7.6 Hz, 1H), 7.8 (d, J=7.3 Hz, 1H).

Example 16

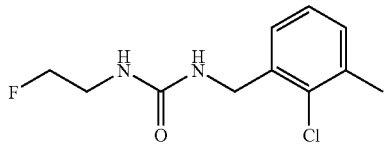 [SMILES: Cc1cccc(CNC(=O)NCCF)c1Cl]

Synthesis of 1-(2-chloro-3-methyl-benzyl)-3-(2-fluoro-ethyl)-urea (Compound 14)

The desired starting amine was prepared from 2-chloro-m-xylene according to the procedures shown in the scheme below. The title compound was thus obtained from this amine according to general procedure B described above.

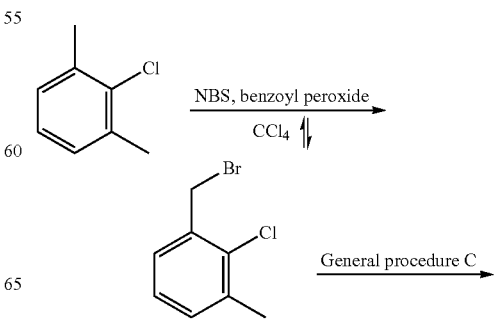

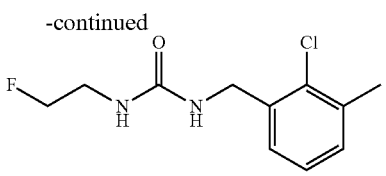

1-Bromomethyl-2-chloro-3-methyl-benzene: A solution of 2-chloro-m-xylene (5.00 g, 35.60 mmol), NBS (5.70 g, 32.03 mmol), and a catalytic amount of benzoyl peroxide (100 mg) in $CCl_4$ was refluxed for 1 hour. After cooling to room temperature the resulting mixture was filtered and the filtrate was distilled off. Purification by column chromatography using pentane as the eluant followed by distillation afforded the title compound. Spectroscopic data: $^1H$ NMR (300 MHz, $CDCl_3$) δ 2.39 (s, 3H), 4.61 (s, 2H), 7.08-7.23 (m, 2H), 7.25-7.30 (m, 1H).

1-Azidomethyl-2-chloro-3-methyl-benzene: The title azido compound was obtained from 1-bromomethyl-2-chloro-3-methyl-benzene (3.68 g, 16.80 mmol) and $NaN_3$ (2.70 g, 41.53 mmol) according to the protocols as outlined in general procedure C above. Spectroscopic data: $^1H$ NMR (300 MHz, $CDCl_3$) δ 2.37-2.45 (s, 3H), 4.49 (s, 2H), 7.15-7.27 (m, 3H).

2-Chloro-3-methyl-benzylamine: The title amine was obtained from 1-azidomethyl-2-chloro-3-methyl-benzene (2.99 g, 16.50 mmol), triphenyl phosphine (4.40 g, 16.78 mmol) and KOH (923 mg, 16.45 mmol) according to the protocols as outlined in general procedure C above.

1-(2-Chloro-3-methyl-benzyl)-3-(2-fluoro-ethyl)-urea: The title urea was obtained from diimidazole carbonyl (1.00 g, 6.16 mmol), fluoroethylamine hydrochloride (640 mg, 90% purity, 5.79 mmol), diisopropyl ethyl amine (2.20 mL, 12.63 mmol) and 2-methyl-cyclohex-2-enylamine (1.00 g, 6.40 mmol) according to the protocols as outlined in general procedure B above. Spectroscopic data: $^1H$ NMR (300 MHz, DMSO-$d_6$) δ 2.32-2.35 (m, 3H), 3.26 (q, J=5.57 Hz, 1H), 3.35 (q, J=5.28, 4.10 Hz, 1H), 4.27 (d, J=6.16 Hz, 2H), 4.31 (t, J=4.98 Hz, 1H), 4.47 (t, J=5.28 Hz, 1H), 6.31 (t, J=5.86, 5.28 Hz, 1H), 6.47 (t, J=6.16 Hz, 1H), 7.13-7.19 (m, 1H), 7.20-7.28 (m, 2H).). $^{13}C$ NMR (75.5 MHz, DMSO-$d_6$) δ 20.60, 31.35, 41.95, 84.00 (d, J=164.06 Hz), 126.73, 127.16, 130.09, 132.77, 136.35, 138.56, 158.48.

Example 17

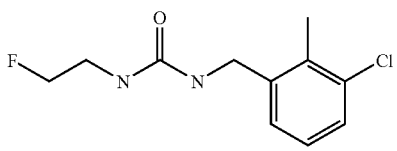 [SMILES: Cc1c(Cl)cccc1CNC(=O)NCCF]

Synthesis of 1-(3-chloro-2-methyl-benzyl)-3-(2-fluoro-ethyl)-urea (Compound 18)

The desired starting amine was prepared from 3-chloro-2-methylbenzoic acid according to the procedures shown in the scheme below. The title compound was thus obtained from this amine according to general procedure B described above.

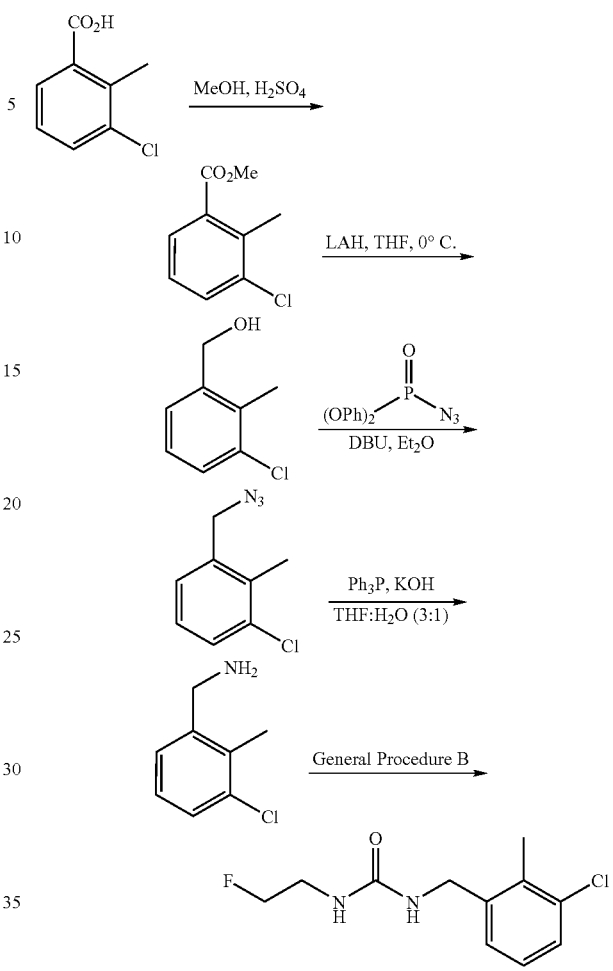

3-Chloro-2-methyl-benzoic acid methyl ester: Approximately two drops of sulfuric acid were added to a solution of 3-chloro-2-methyl-benzoic acid (5.00 g, 29.30 mmol) in methanol and the resulting reaction mixture was refluxed for 14 hours. The reaction mixture was cooled to room temperature, and concentrated, then diluted with EtOAc. The organic layer was washed with saturated $NaHCO_3$ (3×150 mL), $H_2O$ (2×250 mL), brine (1×250 mL) and dried over $MgSO_4$. The crude product was purified by column chromatography using hex:EtOAc (4.5:0.5) as the eluant to give the title ester. Spectroscopic data: $^1H$ NMR (300 MHz, $CDCl_3$) δ 2.60 (s, 3H), 3.90 (s, 3H), 7.16 (t, J=7.325 Hz, 1H), 7.49 (d, J=7.91 Hz, 1H), 7.69 (d, J=7.91 Hz, 1H).

(3-Chloro-2-methyl-phenyl)-methanol: LAH (61.00 mL, 1.0 M in THF, 61.00 mmol) was added to a solution of 3-chloro-2-methyl-benzoic acid methyl ester (4.50 g, 24.40 mmol) in THF at 0° C. The reaction mixture was stirred for 1 hour, water was added to quench the reaction. The aqueous layer was extracted with $Et_2O$ (3×150 mL), and the combined organic phases were washed with brine (1×150 mL) and dried over $MgSO_4$. Purification by column chromatography using hex:EtOAc (4:1) as the eluant afforded 3.97 g of the title compound. Spectroscopic data: $^1H$ NMR (300 MHz, $CDCl_3$) δ 1.94 (br s, 1H), 2.36 (s, 3H), 4.67 (br s, 2H), 7.11 (t, J=7.765 Hz, 1H), 7.245 (d, J=7.03 Hz, 1H), 7.30 (d, J=7.91 Hz, 1H).

1-Azido-3-chloro-2-methyl-benzene: Diphenylphosphoryl azide (6.00 mL, 27.80 mmol) was added to a cooled (0° C.) solution of (3-chloro-2-methyl-phenyl)-methanol (3.66 g, 23.40 mmol) in ether. The resulting mixture was stirred for a few minutes and DBU (4.20 mL, 28.00 mmol) was added slowly. The reaction mixture was stirred for 14 hours, decanted into a clean flask and the residue was washed with more ether. The combined organic phases were concentrated to give the crude title azido compound. Spectroscopic data: $^1$H NMR (300 MHz, CDCl$_3$) δ 2.41 (s, 3H), 4.36 (s, 2H), 7.11-7.26 (m, 2H), 7.35 (dd, J=7.33 Hz, 1H).

3-Chloro-2-methyl-phenylamine: The title amine was obtained from 1-azido-3-chloro-2-methyl-benzene (23.3 mmol), triphenyl phosphine (6.20 g, 23.60 mmol) and KOH (1.3 g, 23.30 mmol) according to the protocols described in general procedure C. Spectroscopic data: $^1$H NMR (300 MHz, CDCl$_3$) δ 1.62 (br s, 2H), 2.37 (s, 3H), 3.85 (br s, 2H), 7.11 (t, J=7.92 Hz, 1H), 7.20 (d, J=6.45 Hz, 1H), 7.27 (d, J=7.62 Hz, 1H).

1-(3-Chloro-2-methyl-benzyl)-3-(2-fluoro-ethyl)-urea: The title urea was obtained from diimidazole carbonyl (1.00 g, 6.16 mmol), fluoroethylamine hydrochloride (640 mg, 90% purity, 5.79 mmol), diisopropyl ethyl amine (2.20 mL, 12.63 mmol) and 3-chloro-2-methyl-phenylamine (1.00 g, 6.40 mmol) according to the protocols described in general procedure B. Spectroscopic data: $^1$H NMR (300 MHz, DMSO-d$_6$) δ 2.28 (s, 3H), 3.24 (q, J=5.28 Hz, 1H), 3.34 (q, J=5.28, 4.40 Hz, 1H), 4.21 (d, J=5.86 Hz, 2H), 4.29 (t, J=4.98 Hz, 1H), 4.44 (t, J=4.98 Hz, 1H), 6.16 (t, J=5.57 Hz, 1H), 6.38 (t, J=5.57 Hz, 1H), 7.12-7.19 (m, 2H), 7.29 (t, J=5.28, 4.10 Hz, 1H). $^{13}$C NMR (75 MHz, DMSO-d$_6$) δ 15.73, 42.27, 84.00 (d, J=164.06 Hz), 126.99, 127.54, 128.05, 133.81, 134.33, 141.58, 158.40.

Example 18

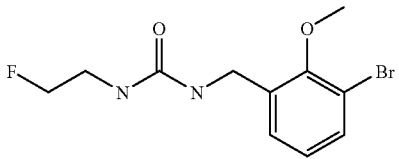 [SMILES: COc1c(Br)cccc1CNC(=O)NCCF]

Synthesis of 1-(3-bromo-2-methoxy-benzyl)-3-(2-fluoro-ethyl)-urea (Compound 19)

The desired starting amine was prepared from 3-bromo-2-methoxybenzoic acid according to the procedures shown in the scheme below. The title compound was thus obtained from this amine according to general procedure B described above.

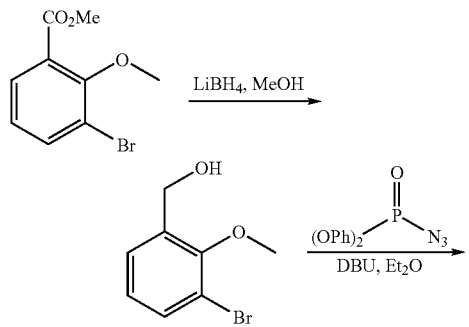

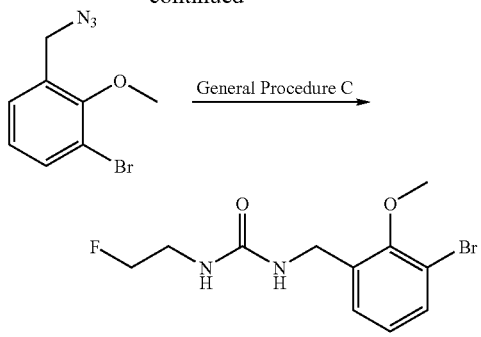

3-Bromo-2-methoxy-benzoic acid methyl ester: Approximately two drops of sulfuric acid were added to a solution of 3-bromo-2-methoxy-benzoic acid (10.00 g, 43.30 mmol) in methanol and the resulting reaction mixture was refluxed for 14 hours. The reaction mixture was cooled to room temperature, and concentrated, then diluted with EtOAc. The organic layer was washed with saturated NaHCO$_3$ (3×150 mL), H$_2$O (2×250 mL), brine (1×250 mL) and dried over MgSO$_4$. The crude product was purified by column chromatography using hex:EtOAc (4.5:0.5) as the eluant to give the title ester. Spectroscopic data: $^1$H NMR (300 MHz, CDCl$_3$) δ 3.91 (s, 3H), 3.94 (s, 3H), 6.92 (d, J=8.79 Hz, 1H), 7.99 (dd, J=8.79 Hz, 1H), 8.24 (d, J=2.35 Hz, 1H).

(3-Bromo-2-methoxy-phenyl)-methanol: LiBH$_4$ (5.00 g, 0.23 mmol) was added to a solution of 3-bromo-2-methoxy-benzoic acid methyl ester (10.50 g, 42.80 mmol) in Et$_2$O at 0° C. The reaction mixture was stirred for 5 minutes, MeOH (8.70 mL, 0.22 mmol) was added in a dropwise fashion. The reaction mixture was then stirred for 30 minutes, and was quenched into 1N NaOH. The resulting solution was extracted with Et$_2$O (3×200 mL) and the combined organic phases were washed with brine (1×150 mL), dried over MgSO$_4$ and concentrated to afford the title compound. Spectroscopic data: $^1$H NMR (300 MHz, CDCl$_3$) δ 1.68 (t, J=5.86 Hz, 1H), 3.90 (s, 3H), 4.61 (d, J=5.86 Hz, 2H), 6.89 (d, J=8.50 Hz, 1H), 7.25-7.30 (m, J=2.00 Hz, 1H), 7.57 (d, J=2.05 Hz, 1H).

1-Azidomethyl-3-bromo-2-methoxy-benzene: Diphenylphosphoryl azide (6.00 mL, 27.80 mmol) was added to a cooled (0° C.) solution of (3-bromo-2-methoxy-phenyl)-methanol (5.00 g, 23.00 mmol) in ether. The resulting mixture was stirred for a few minutes and DBU (4.00 mL, 26.70 mmol) was added slowly. The reaction mixture was stirred for 14 hours, decanted into a clean flask and the residue was washed with more ether. The combined organic phases were concentrated to give the crude title azido compound. Spectroscopic data: $^1$H NMR (300 MHz, CDCl$_3$) δ 3.86 (s, 3H), 4.26 (s, 2H), 6.90 (d, J=8.21 Hz, 1H), 7.18-7.29 (m, 1H), 7.48-7.55 (m, 1H).

3-Bromo-2-methoxy-benzylamine: The title amine was obtained from 1-azidomethyl-3-bromo-2-methoxy-benzene (5.40 g, 22.30 mmol), triphenyl phosphine (6.00 g, 22.88 mmol) and KOH (1.30 g, 23.17 mmol) according to the protocols as outlined in general procedure C. Spectroscopic data: $^1$H NMR (300 MHz, CDCl$_3$) δ 1.62 (br s, 2H), 3.80 (br s, 2H), 3.90 (s, 3H), 6.86 (d, J=8.50 Hz, 1H), 7.21 (dd, J=8.50 Hz, 1H), 7.48-7.53 (m, 1H).

1-(3-Bromo-2-methoxy-benzyl)-3-(2-fluoro-ethyl)-urea: The title urea was obtained from 3-bromo-2-methoxy-benzylamine (1.00 g, 4.60 mmol), diimidazole carbonyl (1.12 g, 6.90 mmol), fluoroethyl amine hydrochloride (460 mg, 90% purity, 4.16 mmol) and diisopropyl ethyl amine (1.60 mL, 9.19 mmol) according to the protocols as outlined in general procedure B. Spectroscopic data: $^1$H NMR (300 MHz, DMSO-d$_6$) δ 3.24 (q, J=5.28 Hz, 1H), 3.33 (q, J=5.28 Hz, 1H), 3.80 (s, 3H), 4.11 (d, J=6.16 Hz, 2H), 4.28 (t, J=5.28 Hz, 1H), 4.45 (t, J=5.28 Hz, 1H), 6.14 (t, J=5.86 Hz, 1H), 6.41 (t, J=5.86 Hz, 1H), 7.02 (d, J=8.50 Hz, 1H), 7.17 (dd, J=8.50 Hz, 1H), 7.40-7.43 (m, 1H). $^{13}$C NMR (75 MHz, DMSO-d$_6$) δ 42.45, 56.82, 83.97 (d, J=164.06 Hz), 110.98, 113.09, 128.33, 132.19, 135.34, 154.77, 158.57.

Example 19

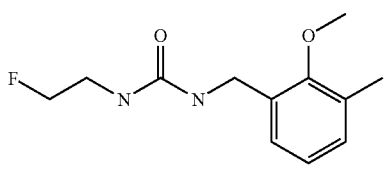 [SMILES: COc1c(C)cccc1CNC(=O)NCCF]

Synthesis of 1-(2-fluoro-ethyl)-3-(2-methoxy-3-methyl-benzyl)-urea (Compound 17)

The desired starting amine was prepared from 2-hydroxy-3-methylbenzoic acid according to the procedures shown in the scheme below. The title compound was thus obtained from this amine according to general procedure B described above.

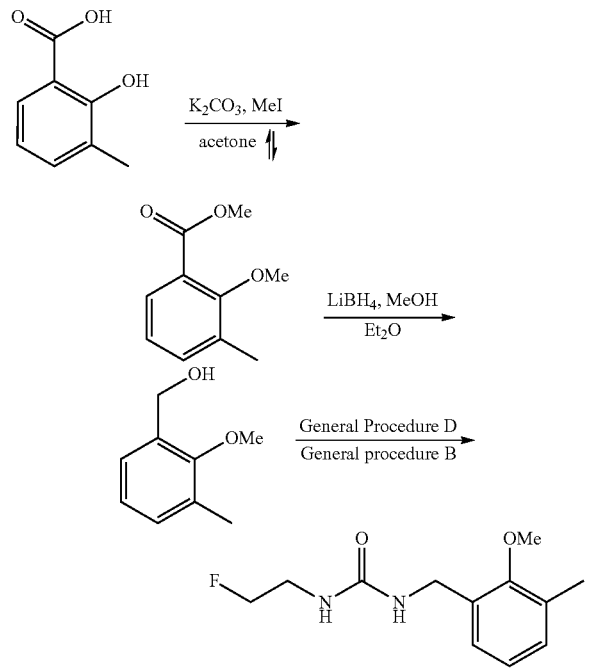

2-Methoxy-3-methyl-benzoic acid methyl ester: Approximately two drops of sulfuric acid were added to a solution of 2-hydroxy-3-methyl-benzoic acid (10.00 g, 65.70 mmol) in methanol and the resulting reaction mixture was refluxed for 14 hours. The reaction mixture was cooled to room temperature, concentrated, and then diluted with EtOAc. The organic layer was washed with saturated NaHCO$_3$ (3×150 mL), H$_2$O (2×250 mL), brine (1×250 mL) and dried over MgSO$_4$. The crude product was purified by column chromatography using hex:EtOAc (4.5:0.5) as the eluant to give the desired ester. This ester was then mixed with MeI (4.50 mL, 72.30 mmol) and K$_2$CO$_3$ (7.50 g, 54.30 mmol) in acetone and the resulting reaction mixture was refluxed for 14 hours. The reaction mixture was cooled to room temperature and then concentrated. The residue was diluted with Et$_2$O. The resulting solution was washed with H$_2$O (3×150 mL) and brine (1×200 mL), then dried over MgSO$_4$ and concentrated. Purification by column chromatography using hex:EtOAc (4:1) as the eluant afforded the title compound. Spectroscopic data: $^1$H NMR (300 MHz, CDCl$_3$) δ 2.30 (s, 3H), 3.83 (s, 3H), 3.92 (s, 3H), 7.06 (t, J=7.92 Hz, 1H), 7.31 (d, J=6.74 Hz, 1H), 7.64 (d, J=8.21 Hz, 1H).

(2-Methoxy-3-methyl-phenyl)-methanol: LiBH$_4$ (5.10 g, 0.23 mmol) was added to a solution of 2-methoxy-3-methyl-benzoic acid methyl ester (8.46 g, 47.00 mmol) in Et$_2$O at 0° C. The reaction mixture was stirred for 5 minutes, MeOH (9.50 mL, 0.23 mmol) was added in a dropwise fashion. The reaction mixture was then stirred for 30 minutes, and was quenched into 1N NaOH. The resulting solution was extracted with Et$_2$O (3×200 mL) and the combined organic phases were washed with brine (1×150 mL), dried over MgSO$_4$ and concentrated to afford the title compound.

1-Azidomethyl-2-methoxy-3-methyl-benzene: The title azido compound was obtained from (2-methoxy-3-methyl-phenyl)-methanol (6.80 g, 44.70 mmol), triethyl amine (12.50 mL, 89.70 mmol), methanesulfonyl chloride (5.20 mL, 67.20 mmol) and NaN$_3$ (7.30 g, 0.11 mol) according to the protocols described in general procedure D. Spectroscopic data: $^1$H NMR (300 MHz, CDCl$_3$) δ 2.31 (s, 3H), 3.76 (s, 3H), 4.37 (s, 2H), 7.03 (t, J=7.33 Hz, 1H), 7.12-7.20 (m, 2H).

2-Methoxy-3-methyl-benzylamine: The title amine was obtained from 1-azidomethyl-2-methoxy-3-methyl-benzene (5.93 g, 33.50 mmol), triphenyl phosphine (8.90 g, 33.93 mmol) and KOH (1.90 g, 33.86 mmol) according to the protocols described in general procedure D. Spectroscopic data: $^1$H NMR (300 MHz, CDCl$_3$) δ 1.82 (br s, 2H), 2.34 (s, 3H), 3.76 (s, 3H), 3.86 (br s, 2H), 7.00 (t, J=7.62 Hz, 1H), 7.06-7.17 (m, 2H).

1-(2-Fluoro-ethyl)-3-(2-methoxy-3-methyl-benzyl)-urea: The title urea was obtained from 2-methoxy-3-methyl-benzylamine (1.00 g, 6.60 mmol), diimidazole carbonyl (1.00 g, 6.16 mmol), fluoroethyl amine hydrochloride (660 mg, 90% purity, 5.97 mmol) and diisopropyl ethyl amine (2.30 mL, 13.20 mmol) according to the protocols described in general procedure B. Spectroscopic data: $^1$H NMR (300 MHz, DMSO-d$_6$) δ 2.19 (s, 3H), 3.23 (q, J=5.28 Hz, 1H), 3.33 (q, J=5.57 Hz, 1H), 3.64 (s, 3H), 4.21 (d, J=5.86 Hz, 2H), 4.29 (t, J=4.98 Hz, 1H), 4.44 (t, J=4.98 Hz, 1H), 6.19 (t, J=5.28 Hz, 1H), 6.30 (t, J=5.86 Hz, 1H), 6.96 (t, J=7.33 Hz, 1H), 7.02-7.10 (m, 2H). $^{13}$C NMR (75 MHz, DMSO-d$_6$) δ 16.33, 38.50, 60.63, 84.04 (d, J=164.06 Hz), 124.42, 126.90, 130.33, 130.94, 133.86, 156.52, 158.54.

Example 20

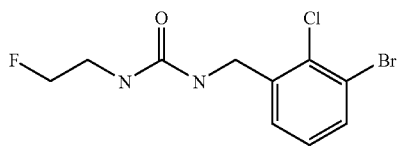 [SMILES: O=C(NCCF)NCc1cccc(Br)c1Cl]

Synthesis of 1-(3-bromo-2-chloro-benzyl)-3-(2-fluoro-ethyl)-urea (Compound 15)

The desired starting amine was prepared from N-(4-bromo-3-chloro-2-methyl-phenyl)-acetamide according to the procedures shown in the scheme below. The title compound was thus obtained from this amine according to general procedure B described above.

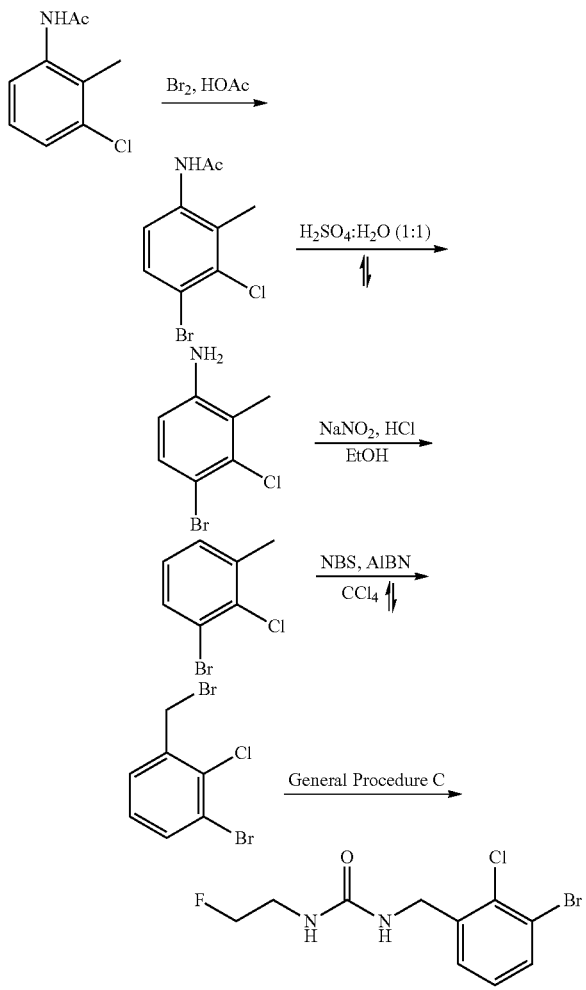

N-(4-Bromo-3-chloro-2-methyl-phenyl)-acetamide: A solution of N-(4-bromo-3-chloro-2-methyl-phenyl)-acetamide (10.00 g, 54.50 mmol) and Br$_2$ (2.80 mL, 54.40 mmol) in HOAc was stirred for 14 hours. The resulting solution was then quenched in H$_2$O and the precipitate was filtered. The precipitate was purified by column chromatography using hex:EtOAc (1:1) as the eluant to afford the title compound. Spectroscopic data: $^1$H NMR (300 MHz, CDCl$_3$) δ 2.19 (s, 3H), 2.35 (s, 3H), 7.06 (br s, 1H), 7.43-7.55 (m, 2H).

4-Bromo-3-chloro-2-methyl-phenylamine: A solution of N-(4-bromo-3-chloro-2-methyl-phenyl)-acetamide (3.37 g, 12.80 mmol) in H$_2$SO$_4$: H$_2$O (1:1) was refluxed for 3 hours. The reaction mixture was cooled to room temperature and neutralized with NaOH and extracted with Et$_2$O (3×150 mL). The combined organic phases were washed with H$_2$O (3×100 mL) and brine (1×100 mL), then dried over MgSO$_4$ and concentrated. Purification by column chromatography using hex:EtOAc (4:1) as the eluant afforded the title aniline. Spectroscopic data: $^1$H NMR (300 MHz, CDCl$_3$) δ 2.31 (s, 3H), 3.93 (br s, 2H), 6.47 (d, J=8.79 Hz, 1H), 7.24 (d, J=7.91 Hz, 1H).

1-Bromo-2-chloro-3-methyl-benzene: Concentrated HCl was added to a solution of 4-bromo-3-chloro-2-methyl-phenylamine (4.98 g, 22.60 mmol) in EtOH. NaNO$_2$ (3.00 g, 43.50 mmol) was added and the resulting mixture was heated to 70° C. for 2 hours. Ethanol was distilled off and the residue was purified by column chromatography using hexanes as the eluant to afford the title compound. Spectroscopic data: $^1$H NMR (300 MHz, CDCl$_3$) δ 2.43 (s, 3H), 7.01 (t, J=7.91 Hz, 1H), 7.18 (d, J=7.62 Hz, 1H), 7.47 (d, J=7.91 Hz, 1H).

1-Bromo-3-bromomethyl-2-chloro-benzene: A solution of 1-bromo-2-chloro-3-methyl-benzene (3.90 g, 19.00 mmol), NBS (3.60 g, 20.20 mmol) and a catalytic amount of AIBN (50 mg) in CCl$_4$ was refluxed for 30 minutes. The reaction mixture was cooled to room temperature and filtered. The precipitate was washed with pentane. The solvent was distilled off and the residue was purified by column chromatography using pentane as the eluant to afford the title compound. Spectroscopic data: $^1$H NMR (300 MHz, CDCl$_3$) δ 4.62 (s, 2H), 7.14 (t, J=7.62 Hz, 1H), 7.39 (dd, J=7.62 Hz, 1H), 7.60 (dd, J=7.91 Hz, 1H).

1-Azidomethyl-3-bromo-2-chloro-benzene: The title azido compound was obtained from 1-bromo-3-bromomethyl-2-chloro-benzene (2.36 g, 8.30 mmol), NaN$_3$ (1.40 g, 21.54 mmol) according to the protocols described in general procedure C above. Spectroscopic data: $^1$H NMR (300 MHz, CDCl$_3$) δ 4.53 (s, 2H), 7.18 (t, J=7.62 Hz, 1H), 7.34-7.39 (m, 1H), 7.63 (dd, J=7.92 Hz, 1H).

3-Bromo-2-chloro-benzylamine: The title amine was obtained from 1-azidomethyl-3-bromo-2-chloro-benzene (2.84 g, 11.50 mmol), triphenyl phosphine (3.00 g, 11.44 mmol) and KOH (650 mg, 11.58 mmol) according to the protocols described in general procedure C above. Spectroscopic data: $^1$H NMR (300 MHz, CDCl$_3$) δ 1.72 (br s, 2H), 3.97 (s, 2H), 7.12 (t, J=7.92 Hz, 1H), 7.32-7.38 (m, 1H), 7.54 (dd, J=7.92 Hz, 1H).

1-(3-Bromo-2-chloro-benzyl)-3-(2-fluoro-ethyl)-urea:
The title urea was obtained from 3-bromo-2-chloro-benzylamine (500 mg, 2.30 mmol), diimidazole carbonyl (370 mg, 2.28 mmol), fluoroethyl amine hydrochloride (225 mg, 90% purity, 2.04 mmol) and diisopropyl ethyl amine (790 μL, 4.54 mmol) according to the protocols described in general procedure B. Spectroscopic data: $^1$H NMR (300 MHz, DMSO-d$_6$) δ 3.26 (q, J=5.28 Hz, 1H), 3.36 (q, J=7.92, 5.28 Hz, 1H), 4.25-4.36 (m, 3H), 4.47 (t, J=5.28 Hz, 1H), 6.36 (t, J=5.57 Hz, 1H), 6.58 (t, J=5.86 Hz, 1H), 7.24-7.36 (m, 2H), 7.60-7.71 (m, 1H). $^{13}$C NMR (75 MHz, DMSO-d$_6$) δ 42.60, 83.95 (d, J=164.06 Hz), 122.91, 128.27, 129.04, 132.19, 132.64, 141.34, 158.42.

Example 21

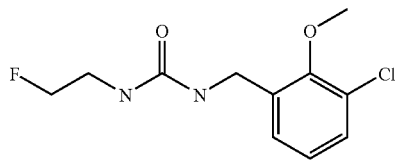 [SMILES: COc1c(Cl)cccc1CNC(=O)NCCF]

Synthesis of 1-(3-chloro-2-methoxy-benzyl)-3-(2-fluoro-ethyl)-urea (Compound 16)

The desired starting amine was prepared from 2-chloro-6-methyl-phenol according to the procedures shown in the scheme below. The title compound was thus obtained from this amine according to general procedure B described above.

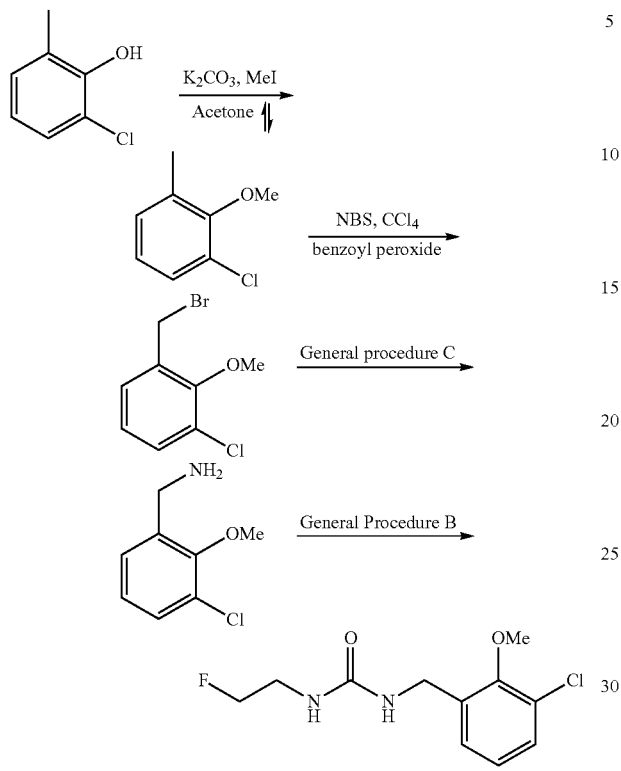

1-Chloro-2-methoxy-3-methyl-benzene: 2-Chloro-6-methyl-phenol (12.00 g, 84.20 mmol) was mixed with MeI (10.50 mL, 0.17 mol) and $K_2CO_3$ (17.40 g, 0.13 mol) in acetone in acetone and the resulting reaction mixture was refluxed for 14 hours. The reaction mixture was cooled to room temperature, and then concentrated. The residue was diluted with $Et_2O$. The resulting solution was washed with $H_2O$ (3×150 mL) and brine (1×200 mL), then dried over $MgSO_4$ and concentrated. Purification by column chromatography using hex:EtOAc (4:1) as the eluant afforded the title compound.

1-Bromomethyl-3-chloro-2-methoxy-benzene: A solution of 1-chloro-2-methoxy-3-methyl-benzene (13.40 g, 85.60 mmol), NBS (15.30 g, 86.00 mmol) and a catalytic amount of benzoyl peroxide (150 mg) in $CCl_4$ was refluxed for 30 minutes. The reaction mixture was cooled to room temperature and filtered. The precipitate was washed with pentane. The solvent was distilled off and the residue was purified by column chromatography using pentane as the eluant to afford the title compound. Spectroscopic data: $^1$H NMR (300 MHz, $CDCl_3$) δ 4.00 (s, 3H), 4.56 (s, 2H), 7.04 (t, J=7.62 Hz, 1H), 7.29 (dd, J=7.62 Hz, 1H), 7.34 (dd, J=7.92 Hz, 1H).

1-Azidomethyl-3-chloro-2-methoxy-benzene: The title azido compound was obtained from 1-bromomethyl-3-chloro-2-methoxy-benzene (18.00 g, 76.40 mmol), $NaN_3$ (12.40 g, 0.19 mol) according to the protocols described in general procedure C above. Spectroscopic data: $^1$H NMR (300 MHz, $CDCl_3$) δ 3.94 (s, 3H), 4.43 (s, 2H), 7.10 (t, J=7.92 Hz, 1H), 7.17-7.28 (m, 1H), 7.37 (dd, J=7.92 Hz, 1H).

3-Chloro-2-methoxy-benzylamine: The title amine was obtained from 1-azidomethyl-3-chloro-2-methoxy-benzene (13.46 g, 68.10 mmol), triphenyl phosphine (19.70 g, 75.11 mmol) and KOH (3.90 g, 69.51 mmol) according to the protocols described in general procedure C above. Spectroscopic data: $^1$H NMR (300 MHz, $CDCl_3$) δ 1.67 (br s, 2H), 3.87 (br s, 2H), 3.89 (s, 3H), 7.03 (t, J=7.62 Hz, 1H), 7.19-7.23 (m, 1H), 7.28 (t, J=7.92 Hz, 1H).

1-(3-Chloro-2-methoxy-benzyl)-3-(2-fluoro-ethyl)-urea: The title urea was obtained from 3-chloro-2-methoxy-benzylamine (2.00 g, 11.70 mmol), diimidazole carbonyl (1.90 g, 11.71 mmol), fluoroethyl amine hydrochloride (1.20 g, 90% purity, 10.85 mmol) and diisopropyl ethyl amine (4.00 mL, 22.97 mmol) according to the protocols described in general procedure B above. Spectroscopic data: $^1$H NMR (300 MHz, DMSO-$d_6$) δ 3.24 (q, J=5.28 Hz, 1H), 3.34 (q, J=5.28 Hz, 1H), 3.75 (s, 3H), 4.18-4.32 (m, 3H), 4.43 (t, J=4.98 Hz, 1H), 6.23 (t, J=5.86 Hz, 1H), 6.41 (t, J=5.86 Hz, 1H), 7.09 (t, J=7.92 Hz, 1H), 7.19 (d, J=7.04 Hz, 1H), 7.32 (d, J=7.62 Hz, 1H). $^{13}$C NMR (75 MHz, DMSO-$d_6$) δ 38.56, 61.17, 84.00 (d, J=164.06 Hz), 125.77, 127.22, 128.11, 129.27, 136.76, 153.70, 158.51.

Example 22

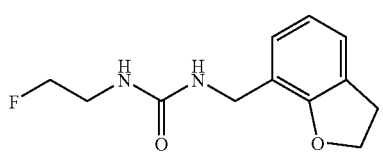 [SMILES: O=C(NCCF)NCc1cccc2c1OCC2]

Synthesis of 1-(2,3-dihydro-benzofuran-7-ylmethyl)-3-(2-fluoro-ethyl)-urea (Compound 20)

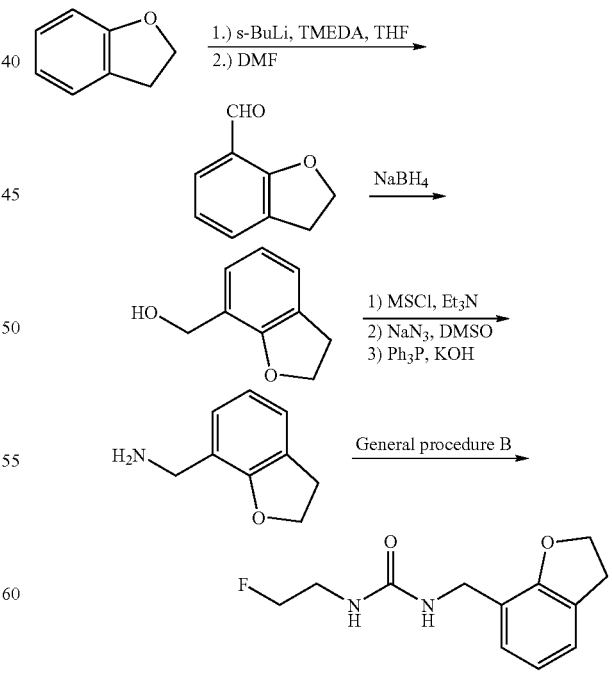

2,3-Dihydro-benzofuran-7-carbaldehyde: sec-BuLi (20.00 ml, 1.4 M in cyclohexane, 28.00 mmol) was added to a solution of 2,3-dihydro-benzofuran (2.40 mL, 21.30 mmol)

and tetramethylethylenediamine (TMEDA, 10.00 mL) in THF at −20° C. The resulting mixture was stirred for 1 hour, then DMF (3.00 mL, 38.75 mmol) was added and stirring was continued for another 30 minutes. The reaction mixture was quenched with water and diluted with ether. The resulting solution was washed with brine, dried over MgSO$_4$ and concentrated to afford the desired title aldehyde.

(2,3-Dihydro-benzofuran-7-yl)-methanol: The title alcohol was obtained from 2,3-Dihydro-benzofuran-7-carbaldehyde (1.50 g, 10.20 mmol) and NaBH$_4$ (400 mg, 10.57 mmol) according to the protocols as outlined in general procedure D.

C-(2,3-Dihydro-benzofuran-7-yl)-methylamine: The title amine was obtained from (2,3-dihydro-benzofuran-7-yl)-methanol (1.50 g, 10.00 mmol), MsCl (1.30 mL, 16.80 mmol), Et$_3$N (3.0 mL, 21.52 mmol), NaN$_3$ (1.30 g, 20.00 mmol), Ph$_3$P (2.70 g, 10.29 mmol) and KOH (600 mg, 10.69 mmol) according to the protocols as outlined in general procedure D.

1-(2,3-Dihydro-benzofuran-7-ylmethyl)-3-(2-fluoro-ethyl)-urea: The title compound was obtained from 1-(2,3-dihydro-benzofuran-7-yl)-methylamine (1.50 g, 10.0-mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-d$_6$) δ 3.01-3.46 (m, 4H), 4.1 (d, J=5.9 Hz, 2H), 4.3 (t, J=5.0 Hz, 1H), 4.44-4.58 (m, 3H), 6.2 (t, J=5.6 Hz, 1H), 6.3 (t, J=5.6 Hz, 1H), 6.8 (t, J=7.6 Hz, 1H), 7.0 (d, J=7.6 Hz, 1H), 7.1 (d, J=7.0 Hz, 1H).

Example 23

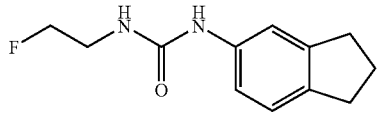 [SMILES: O=C(NCCF)Nc1ccc2c(c1)CCC2]

Synthesis of 1-(2-fluoro-ethyl)-3-indan-5-yl-urea (Compound 21)

1-(2-Fluoro-ethyl)-3-indan-5-yl-urea: The title compound was obtained from indan-5-ylamine (1.30 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-d$_6$) δ 1.90-2.04 (m, 2H), 2.8 (q, J=8.8, 7.6 Hz, 4H), 3.28-3.37 (m, 2H), 3.4 (q, J=5.3 Hz, 1H), 4.4 (t, J=5.3, 4.7 Hz, 1H), 4.5 (t, J=5.3 Hz, 1H), 6.3 (t, J=5.6 Hz, 1H), 7.1 (s, 1H), 7.3 (s, 1H), 8.4 (s, 1H).

Example 24

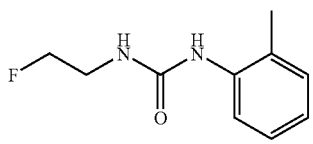

Synthesis of 1-(2-fluoro-ethyl)-3-o-tolyl-urea (Compound 22)

1-(2-Fluoro-ethyl)-3-o-tolyl-urea: The title compound was obtained from 1-isocyanato-2-methyl-benzene (1.20 g, 9.00 mmol), fluoroethyl amine hydrochloride (1.00 g, 90% purity, 9.05 mmol) and diisopropylethyl amine (3.20 mL, 18.37 mmol) according to the protocols as outlined in general procedure A above. Spectroscopic data: $^1$H NMR (300 MHz, DMSO-d$_6$) δ ppm 2.16 (s, 3H) 3.34 (q, J=5.28 Hz, 1H) 3.43 (q, J=5.28 Hz, 1H) 4.37 (t, J=4.98 Hz, 1H) 4.53 (t, J=4.98 Hz, 1H) 6.78 (t, J=5.42 Hz, 1H) 6.86 (td, J=7.40, 1.32 Hz, 1H) 7.02-7.15 (m, 2H) 7.70 (s, 1H) 7.74-7.82 (m, 1H).

Example 25

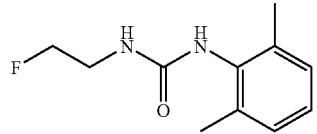

Synthesis of 1-(2,6-dimethyl-phenyl)-3-(2-fluoro-ethyl)-urea (Compound 23)

1-(2,6-Dimethyl-phenyl)-3-(2-fluoro-ethyl)-urea: The title compound was obtained from 2-isocyanato-1,3-dimethyl-benzene (1.30 g, 8.80 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-d$_6$) δ ppm 2.14 (s, 6H) 3.23-3.34 (m, 1H) 3.38 (q, J=5.08 Hz, 1H) 4.33 (t, J=5.13 Hz, 1H) 4.49 (t, J=4.98 Hz, 1H) 6.24 (s, 1H) 6.94-7.06 (m, 3H) 7.53 (s, 1H).

Example 26

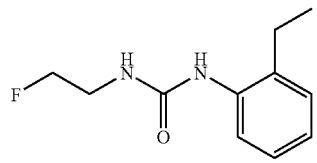

Synthesis of 1-(2-ethyl-phenyl)-3-(2-fluoro-ethyl)-urea (Compound 24)

1-(2-Ethyl-phenyl)-3-(2-fluoro-ethyl)-urea: The title compound was obtained from 1-ethyl-2-isocyanato-benzene (1.30 g, 8.80 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-d$_6$) δ ppm 1.11 (t, J=7.48 Hz, 3H) 2.49-2.59 (m, 2H) 3.25-3.38 (m, 1H) 3.43 (q, J=5.18 Hz, 1H) 4.37 (t, J=4.98 Hz, 1H) 4.53 (t, J=4.98 Hz, 1H) 6.78 (t, J=5.42 Hz, 1H) 6.91 (td, J=7.40, 1.32 Hz, 1H) 7.03-7.16 (m, 2H) 7.69 (s, 1H) 7.72-7.80 (m, 1H).

Example 27

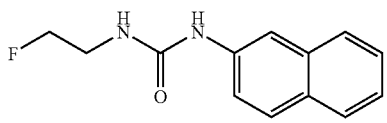 [SMILES: O=C(NCCF)Nc1ccc2ccccc2c1]

Synthesis of 1-(2-fluoro-ethyl)-3-naphthalen-2-yl-urea (Compound 25)

1-(2-Fluoro-ethyl)-3-naphthalen-2-yl-urea: The title compound was obtained from 2-isocyanato-naphthalene (1.40 g, 8.30 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-$d_6$) δ ppm 3.35-3.45 (m, 1H) 3.50 (q, J=5.18 Hz, 1H) 4.42 (t, J=4.69 Hz, 1H) 4.58 (t, J=4.98 Hz, 1H) 6.88 (s, 1H) 7.41 (t, J=7.77 Hz, 1H) 7.46-7.58 (m, 3H) 7.88 (d, J=7.04 Hz, 1H) 7.99 (d, J=7.62 Hz, 1H) 8.09 (d, J=7.62 Hz, 1H) 8.63 (s, 1H).

Example 28

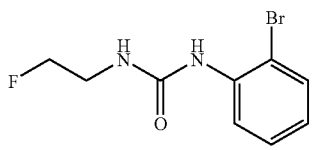 [SMILES: O=C(NCCF)Nc1ccccc1Br]

Synthesis of 1-(2-bromo-phenyl)-3-(2-fluoro-ethyl)-urea (Compound 26)

1-(2-Bromo-phenyl)-3-(2-fluoro-ethyl)-urea: The title compound was obtained from 1-bromo-2-isocyanato-benzene (1.70 g, 8.60 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^1$H NMR (300 MHz, DMSO-$d_6$) δ ppm 3.35 (q, J=4.98 Hz, 1H) 3.44 (q, J=5.18 Hz, 1H) 4.38 (t, J=4.98 Hz, 1H) 4.54 (t, J=4.98 Hz, 1H) 6.88 (td, J=7.62, 1.76 Hz, 1H) 7.19-7.30 (m, 1H) 7.33 (t, J=5.42 Hz, 1H) 7.54 (dd, J=7.92, 1.47 Hz, 1H) 7.91 (s, 1H) 8.03 (dd, J=8.36, 1.61 Hz, 1H).

Example 29

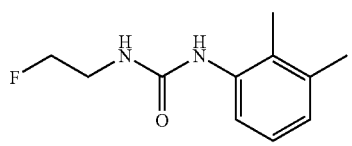

Synthesis of 1-(2,3-dimethyl-phenyl)-3-(2-fluoro-ethyl)-urea (Compound 27)

1-(2,3-Dimethyl-phenyl)-3-(2-fluoro-ethyl)-urea: The title compound was obtained from 1-isocyanato-2,3-dimethyl-benzene (1.30 g, 8.80 mmol), fluoroethyl amine hydrochloride (1.00 g, 90% purity, 9.05 mmol) and diisopropylethyl amine (3.00 mL, 17.22 mmol) according to the protocols as outlined in general procedure A above. Spectroscopic data: $^{13}$C NMR (75 MHz, DMSO-$d_6$) δ 14.2, 21.0, 40.4 (d, J=20.7 Hz), 83.9 (d, J=164.1 Hz), 120.6, 125.0, 125.8, 127.5, 137.0, 138.3, 156.3.

Example 30

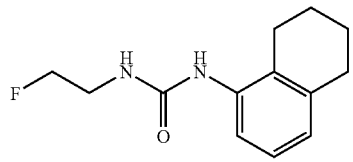 [SMILES: O=C(NCCF)Nc1cccc2c1CCCC2]

Synthesis of 1-(2-fluoro-ethyl)-3-(5,6,7,8-tetrahydro-naphthalen-1-yl)-urea (Compound 28)

1-(2-Fluoro-ethyl)-3-(5,6,7,8-tetrahydro-naphthalen-1-yl)-urea: The title compound was obtained 5,6,7,8-tetrahydro-naphthalen-1-ylamine (1.50 g, 10.20 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 1.64-1.80 (m, 4H), 2.44-2.58 (m, 2H), 2.64-2.74 (m, 2H), 3.31-3.47 (m, 2H), 4.30-4.44 (m, 1H), 4.49-4.58 (m, 1H), 6.7 (d, J=7.3 Hz, 1H), 6.76-6.84 (m, 1H), 7.0 (t, J=7.9, 7.0 Hz, 1H), 7.55-7.67 (m, 2H).

Example 31

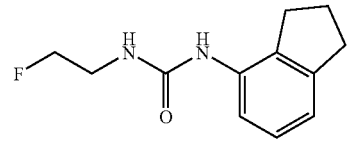 [SMILES: O=C(NCCF)Nc1cccc2c1CCC2]

Synthesis of 1-(2-fluoro-ethyl)-3-indan-4-yl-urea (Compound 29)

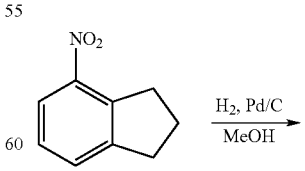

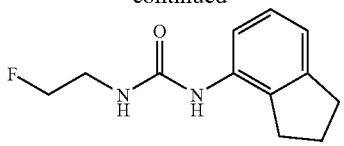

Indan-4-ylamine: 4-Nitro-indan (5.00 g, 30.70 mmol) was dissolved in methanol, and Pd/C (500 mg) was added. The resulting reaction mixture was hydrogenated at 50 psi for 14 hours. Filtration through celite and concentration afforded the title indan-4-yl-amine.

1-(2-Fluoro-ethyl)-3-indan-4-yl-urea: The title compound was obtained from indan-4-ylamine (1.30 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 1.94-2.08 (m, 2H), 2.7 (t, J=7.0 Hz, 2H), 2.8 (t, J=7.6 Hz, 2H), 3.32-3.48 (m, 2H), 4.4 (t, J=5.3, 4.7 Hz, 1H), 4.5 (t, J=5.0 Hz, 1H), 6.73-6.86 (m, 2H), 6.96-7.09 (m, 1H), 7.68-7.76 (m, 1H), 7.79-7.85 (m, 1H).

Example 32

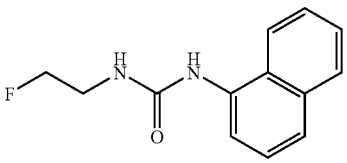 [SMILES: O=C(NCCF)Nc1cccc2ccccc12]

Synthesis of 1-(2-fluoro-ethyl)-3-naphthalen-1-yl-urea (Compound 30)

1-(2-Fluoro-ethyl)-3-naphthalen-1-yl-urea: The title compound was obtained from naphthalen-1-ylamine (1.40 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.39-3.45 (m, 1H), 3.48-3.63 (m, 1H), 4.4 (t, J=5.0 Hz, 1H), 4.6 (t, J=5.3 Hz, 1H), 6.9 (t, J=6.4 Hz, 1H), 7.4 (t, J=7.9 Hz, 1H), 7.48-7.59 (m, 3H), 7.86-7.93 (m, 1H), 8.0 (d, J=7.6 Hz, 1H), 8.1 (d, J=7.9 Hz, 1H), 8.6 (s, 1H).

Example 33

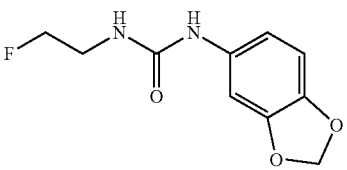 [SMILES: O=C(NCCF)Nc1ccc2c(c1)OCO2]

Synthesis of 1-benzo(1,3)dioxol-4-ylmethyl-3-(2-fluoro-ethyl)-urea (Compound 31)

Benzo(1,3)dioxol-4-yl-methanol: The title alcohol was obtained from benzo(1,3)dioxole-4-carbaldehyde (5.00 g, 33.30 mmol) and NaBH$_4$ (1.30 g, 34.34 mmol) according to the protocols as outlined in general procedure D.

1-Benzo(1,3)dioxol-4-yl-methylamine: The title amine was obtained from benzo(1,3)dioxol-4-yl-methanol, MsCl (4.00 mL, 51.68 mmol), Et$_3$N (9.30 mL, 66.72 mmol), NaN$_3$ (4.30 g, 66.14 mmol), Ph$_3$P (9.00 g, 34.31 mmol) and KOH (1.90 g, 33.86 mmol) according to the protocols as outlined in general procedure D.

1-Benzo(1,3)dioxol-4-ylmethyl-3-(2-fluoro-ethyl)-urea: The title compound was obtained from 1-benzo(1,3)dioxol-4-yl-methylamine (1.50 g, 10.00 mmol), diimidazole carbonyl (1.70 g, 10.48 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-$d_6$) δ 3.23-3.39 (m, 2H), 4.2 (d, J=5.9 Hz, 2H), 4.3 (t, J=5.0 Hz, 1H), 4.5 (t, J=5.0 Hz, 1H), 6.0 (s, 2H), 6.2 (t, J=5.9 Hz, 1H), 6.4 (t, J=5.9 Hz, 1H), 6.73-6.84 (m, 3H). $^{13}$C NMR (75 MHz, DMSO-$d_6$) δ 37.9, 40.6 (d, J=20.7 Hz), 84.0 (d, J=165.2 Hz), 101.3, 107.7, 121.6, 122.0, 122.5, 145.1, 147.4, 158.6.

Example 34

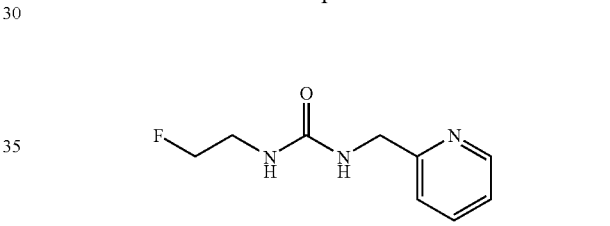

Synthesis of 1-(2-fluoro-ethyl)-3-pyridin-2-ylmethyl-urea (Compound 35)

1-(2-Fluoro-ethyl)-3-pyridin-2-ylmethyl-urea: The title compound was obtained from 2-aminomethylpyridine (826 mg, 7.60 mmol), diimidazole carbonyl (1.29 g, 7.95 mmol), fluoroethyl amine hydrochloride (840 mg, 90% purity, 7.60 mmol) and diisopropylethyl amine (2.50 ml, 14.35 mmol) according to the protocols as outlined in general procedure B as above. Spectroscopic data: $^1$H NMR (300 MHz, Acetone-$d_6$) δ 3.41 (q, J=5.47 Hz, 1H) 3.49 (q, J=5.37 Hz, 1H) 4.36 (t, J=5.13 Hz, 1H) 4.43 (d, J=5.86 Hz, 2H) 4.52 (t, J=5.13 Hz, 1H) 6.05 (s, 1H) 6.19 (s, 1H) 7.18-7.23 (m, 1H) 7.33 (d, J=7.32 Hz, 1H) 7.72 (t, J=7.62 Hz, 1H) 8.47 (d, J=4.7 Hz, 1H).

Example 35

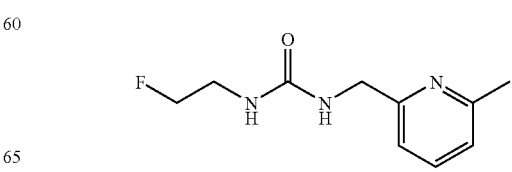

Synthesis of 1-(2-fluoro-ethyl)-3-(6-methyl-pyridin-2-ylmethyl)-urea (Compound 36)

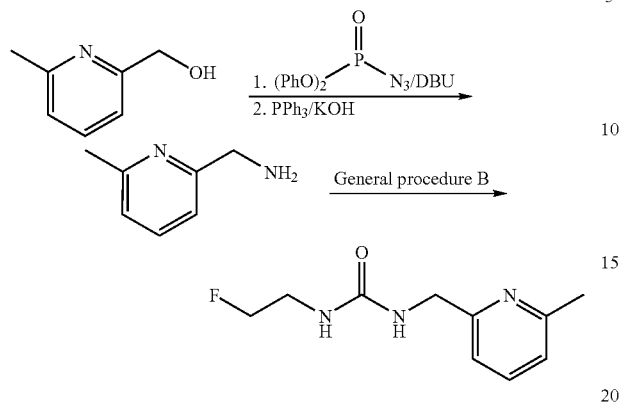

General procedure B

6-Methyl-2-aminomethylpyridine: Diphenylphosphoryl azide (8.02 g, 29.16 mmol) was added to a cooled (0° C.) solution of 6-methyl2-pyridinemethanol (3.00 g, 24.30 mmol) in ether. The resulting mixture was stirred for a few minutes and DBU (4.07 g, 26.73 mmol) was added slowly. The reaction mixture was stirred for 14 hours, decanted into a clean flask and the residue was washed with more ether. The combined organic phases were concentrated to give the crude title azido compound. The crude azide was dissolved in THF:$H_2O$ (3:1) and $Ph_3P$ (5.77 g, 22.00 mmol) was added, followed by KOH (1.23 g, 22.00 mmol). The reaction mixture was stirred for 14 hours, and then was acidified with concentrated HCl. The resulting solution was washed with $Et_2O$ and the aqueous layer was basified with $NH_3$ and extracted with $Et_2O$ (3×200 mL). The combined organic extracts were washed with $H_2O$ (3×100 mL) and brine (1×100 mL), then dried over $MgSO_4$ and concentrated to give the desired substituted benzylamine. Spectroscopic data: $^1$H NMR (300 MHz, Acetone-$d_6$) δ 2.52 (s, 3H) 3.91 (s, 2H) 7.04 (d, J=7.61 Hz, 1H) 7.05 (d, J=7.90 Hz, 1H) 7.51 (t, J=7.82 Hz, 1H).

1-(2-Fluoro-ethyl)-3-(6-methyl-pyridin-2-ylmethyl)-urea: The title compound was obtained from 6-methyl-2-aminomethylpyridine (600 mg, 2.95 mmol), diimidazole carbonyl (502 mg, 3.09 mmol), fluoroethyl amine hydrochloride (326 mg, 90% purity, 2.95 mmol) and diisopropylethyl amine (1.20 ml, 6.89 mmol) according to the protocols as outlined in general procedure B above. Spectroscopic data: $^1$H NMR (300 MHz, Acetone-$d_6$) δ 2.45 (s, 3H) 3.41 (q, J=5.47 Hz, 1H) 3.49 (q, J=5.37 Hz, 1H) 4.31-4.41 (m, 3H) 4.52 (t, J=5.13 Hz, 1H) 6.08 (s, 1H) 6.19 (s, 1H) 7.10 (dd, J=14.66, 7.62 Hz, 2H) 7.59 (t, J=7.62 Hz, 1H).

Example 36

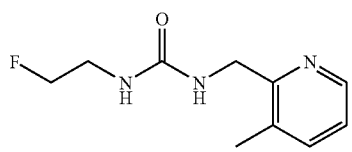

Synthesis of 1-(2-fluoro-ethyl)-3-(3-methyl-pyridin-2-ylmethyl)-urea (Compound 37)

1-(2-Fluoro-ethyl)-3-(3-methyl-pyridin-2-ylmethyl)-urea: The title compound was obtained from 3-methyl 2-aminomethylpyridine (928 mg, 7.60 mmol), diimidazole carbonyl (1.29 g, 7.95 mmol), fluoroethyl amine hydrochloride (840 mg, 90% purity, 7.60 mmol) and diisopropylethyl amine (2.50 ml, 14.35 mmol) according to the protocols as outlined in general procedure B above. Spectroscopic data: $^1$H NMR (300 MHz, Acetone-$d_6$) δ 2.29 (s, 3H) 3.43 (q, J=5.47 Hz, 1H) 3.52 (q, J=5.28 Hz, 1H) 4.37 (t, J=5.13 Hz, 1H) 4.43 (d, J=4.40 Hz, 2H) 4.53 (t, J=5.13 Hz, 1H) 6.40 (s, 1H) 6.50 (s, 1H) 7.15 (dd, J=7.48, 4.84 Hz, 1H) 7.53 (d, J=7.62 Hz, 1H) 8.31 (d, J=4.69 Hz, 1H).

Example 37

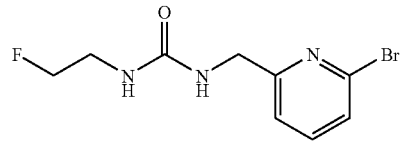 [SMILES: O=C(NCCF)NCc1cccc(Br)n1]

Synthesis of 1-(6-bromo-pyridin-2-ylmethyl)-3-(2-fluoro-ethyl)-urea (Compound 38)

The desired amine precursor was obtained from the commercially available (6-bromo-pyridin-2-yl)methanol according to the protocols described in the following scheme. The title compound was thus afforded from this amine according to general procedure B above. The intermediates 2-bromo-6-bromomethyl-pyridine and 6-bromo-2-aminomethylpyridine were separated and characterized.

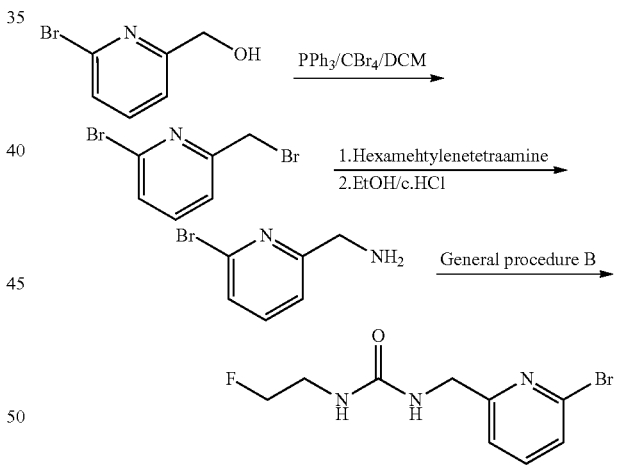

2-Bromo-6-bromomethyl-pyridin: Carbon tetrabromide (12.90 g, 38.88 mmol) was added in four portions to a solution of (6-bromo-pyridin-2-yl)methanol (5.00 g, 29.91 mmol) and $PPh_3$ (8.24 g, 31.40 mmol) in dichloromethane (50 ml) at 0° C. The resulting solution was stirred 2 hours at 0° C. Solvent was removed under reduced pressure. The title compound was obtained by column chromatography. Spectroscopic data: $^1$H NMR (300 MHz, Acetone-$d_6$) δ 4.66 (s, 2H) 7.57-7.60 (m, 2H) 7.76 (t, J=7.42 Hz, 1H).

6-Bromo-2-aminomethylpyridine: 2-Bromo-6-bromomethyl-pyridine (2.67 g, 10.63 mmol) was combined with hexamethylenetetramine (3.00 g, 21.30 mmol) in chloroform (50 ml) and the resulting reaction mixture was stirred at reflux for 14 hours. The reaction mixture was then cooled to room temperature and the white solid was collected by filtration. The white solid was suspended in ethanol (50 ml) and concentrated HCl (12 ml) was added. The resulting reaction mixture was stirred at 90° C. for 14 hours. Adjustment of pH to 12 was done by the addition of aq 5N NaOH. The reaction mixture was extracted with dichloromethane several times. The combined organic layers were concentrated to yield the title compound. Spectroscopic data: $^1$H NMR (300 MHz, CDCl$_3$) δ 3.95 (s, 2H) 7.19-7.28 (m, 2H) 7.62 (t, J=7.82 Hz, 1H).

1-(6-Bromo-pyridin-2-ylmethyl)-3-(2-fluoro-ethyl)-urea: The title compound was obtained from 6-bromo-2-aminomethylpyridine (929 mg, 4.97 mmol), diimidazole carbonyl (845 mg, 5.21 mmol), fluoroethyl amine hydrochloride (550 mg, 90% purity, 4.97 mmol) and diisopropylethyl amine (1.80 ml, 10.33 mmol) according to the protocols as outlined in general procedure B above. Spectroscopic data: $^1$H NMR (300 MHz, Acetone-d$_6$) δ 3.40 (q, J=5.47 Hz, 1H) 3.49 (q, J=5.28 Hz, 1H) 4.34 (t, J=5.13 Hz, 1H) 4.40 (d, J=4.40 Hz, 2H) 4.52 (t, J=5.13 Hz, 1H) 6.07 (s, 1H) 6.27 (s, 1H) 7.29 (d, J=7.90 Hz, 1H) 7.34 (d, J=7.90 Hz, 1H) 7.78 (t, J=7.9 Hz, 1H).

Example 38

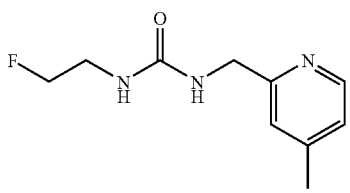

Synthesis of 1-(2-Fluoro-ethyl)-3-(4-methyl-pyridin-2-ylmethyl)-urea (Compound 39)

The desired amine precursor was obtained from the commercially available 2-cyano-4-methylpyridine according to the protocols described in the following scheme. The title compound was thus afforded from this amine according to general procedure B above. The intermediate 4-methyl-2-aminomethylpyridine was separated and characterized.

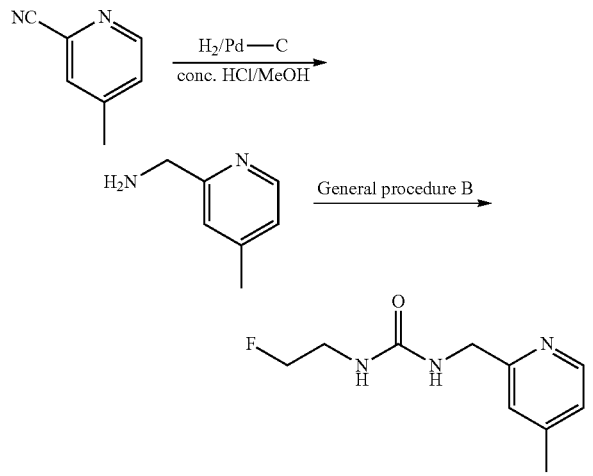

4-Methyl-2-aminomethylpyridine: 2-Cyano 4-methylpyridine in MeOH (35 ml) and concentrated HCl (1 ml) was stirred under a H$_2$ balloon for 14 hours. The reaction mixture was filtered and concentrated. The pH was adjusted to 12 by the addition of aq sodium hydroxide. The resulting reaction mixture was extracted with dichloromethane several times. Concentration of the solvent gave the crude title compound, which was used in the next step without further purification.

1-(2-Fluoro-ethyl)-3-(4-methyl-pyridin-2-ylmethyl)-urea: The title compound was obtained from 4-methyl 2-aminomethylpyridine (400 mg, crude, taken from the previous step, 3.27 mmol), diimidazole carbonyl (650 mg, 4.01 mmol), fluoroethyl amine hydrochloride (420 mg, 90% purity, 3.80 mmol) and diisopropylethyl amine (1.20 ml, 6.89 mmol) according to the protocols as outlined in general procedure B above. Spectroscopic data: $^1$H NMR (300 MHz, Acetone-d$_6$) δ 2.29 (s, 3H) 3.43 (q, J=5.47 Hz, 1H) 3.52 (q, J=5.28 Hz, 1H) 4.37 (t, J=5.13 Hz, 1H) 4.43 (d, J=4.40 Hz, 2H) 4.53 (t, J=5.13 Hz, 1H) 6.40 (s, 1H) 6.50 (s, 1H) 7.15 (dd, J=7.48, 4.84 Hz, 1H) 7.53 (d, J=7.62 Hz, 1H) 8.31 (d, J=4.69 Hz, 1H).

Example 39

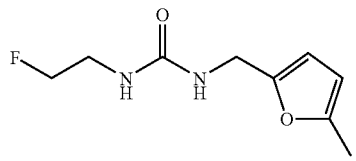

Synthesis of 1-(2-fluoro-ethyl)-3-(5-methyl-furan-2-ylmethyl)-urea (Compound 40)

The title compound was obtained from the commercially available 5-methylfurfurylamine according to general procedure B described above.

1-(2-Fluoro-ethyl)-3-(5-methyl-furan-2-ylmethyl)-urea: The title compound was obtained from 5-methylfurfurylamine (550 mg, 4.97 mmol), diimidazole carbonyl (845 mg, 5.21 mmol), fluoroethyl amine hydrochloride (550 mg, 90% purity, 4.97 mmol) and diisopropylethyl amine (1.80 ml, 10.33 mmol) according to the protocols as outlined in general procedure B above. Spectroscopic data: $^1$H NMR (300 MHz, Acetone-d$_6$) δ 2.21 (s, 3H) 3.37 (q, J=5.47 Hz, 1H) 3.47 (q, J=5.28 Hz, 1H) 4.24 (d, J=5.50 Hz, 2H) 4.34 (t, J=5.13 Hz, 1H) 4.50 (t, J=5.13 Hz, 1H) 5.80-6.08 (m, 4H).

Example 40

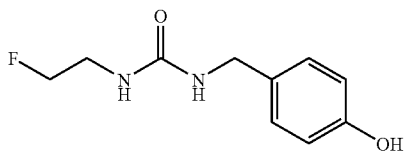 [SMILES: O=C(NCCF)NCc1ccc(O)cc1]

Synthesis of 1-(2-fluoro-ethyl)-3-(4-hydroxy-benzyl)-urea (Compound 41)

The title compound was obtained from the commercially available 4-hydroxybenzylamine according to general procedure B described above.

1-(2-Fluoro-ethyl)-3-(4-hydroxy-benzyl)-urea: The title compound was obtained from 4-hydroxy benzylamine (935 mg, 7.60 mmol), diimidazole carbonyl (1.29 g, 7.95 mmol), fluoroethyl amine hydrochloride (840 mg, 90% purity, 7.60 mmol) and diisopropylethyl amine (2.50 ml, 15.35 mmol) according to the protocols as outlined in general procedure B above. Spectroscopic data: $^1$H NMR (300 MHz, Acetone-$d_6$) δ 3.38 (q, J=5.47 Hz, 1H) 3.49 (q, J=5.28 Hz, 1H) 4.23 (d, J=5.7 Hz, 2H) 4.34 (t, J=5.13 Hz, 1H) 4.49 (t, J=5.13 Hz, 1H) 6.20 (s, 1H) 6.30 (s, 1H) 6.79 (d, J=8.52 Hz, 2H) 7.14 (d, J=8.52 Hz, 2H) 8.72 (s, 1H).

Example 41

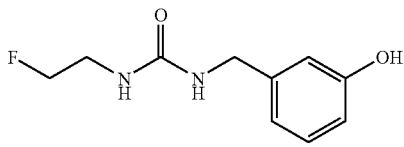 [SMILES: O=C(NCCF)NCc1cccc(O)c1]

Synthesis of 1-(2-fluoro-ethyl)-3-(3-hydroxy-benzyl)-urea (Compound 42)

The title compound was obtained from the commercially available 3-hydroxybenzylamine according to general procedure B described above.

1-(2-Fluoro-ethyl)-3-(3-hydroxy-benzyl)-urea: The title compound was obtained from 3-hydroxy benzylamine (935 mg, 7.60 mmol), diimidazole carbonyl (1.29 g, 7.95 mmol), fluoroethyl amine hydrochloride (840 mg, 90% purity, 7.60 mmol) and diisopropylethyl amine (2.50 ml, 15.35 mmol) according to the protocols as outlined in general procedure B above. Spectroscopic data: $^1$H NMR (300 MHz, Acetone-$d_6$) δ 3.38 (q, J=5.47 Hz, 1H) 3.49 (q, J=5.28 Hz, 1H) 4.27 (d, J=5.7 Hz, 2H) 4.35 (t, J=5.13 Hz, 1H) 4.51 (t, J=5.13 Hz, 1H) 5.92 (s, 1H) 6.05 (s, 1H) 6.67-6.80 (m, 3H) 7.10 (t, J=7.92 Hz, 1H) 8.40 (s, 1H).

Example 42

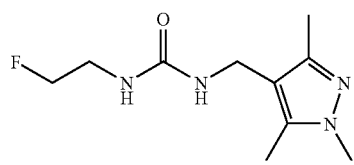 [SMILES: Cc1nn(C)c(C)c1CNC(=O)NCCF]

Synthesis of 1-(2-fluoro-ethyl)-3-(1,3,5-trimethyl-1H-pyrazol-4-ylmethyl)-urea (Compound 43)

The title compound was obtained from the commercially available 1,3,5-trimethyl-1H-pyrazol-4-yl)methylamine according to general procedure B described above.

1-(2-Fluoro-ethyl)-3-(1,3,5-trimethyl-1H-pyrazol-4-ylmethyl)-urea: The title compound was obtained from 1,3,5-trimethyl-1H-pyrazol-4-yl)methylamine (917 mg, 6.60 mmol), diimidazole carbonyl (1.07 g, 6.59 mmol), fluoroethyl amine hydrochloride (729 mg, 90% purity, 6.59 mmol) and diisopropylethyl amine (2.3 ml, 13.20 mmol) according to the protocols as outlined in general procedure B above.

Spectroscopic data: $^1$H NMR (300 MHz, Acetone-$d_6$) δ 2.08 (s, 3H) 2.18 9s, 3H) 3.34 (q, J=5.47 Hz, 1H) 3.45 (q, J=5.28 Hz, 1H) 3.61 (s, 3H) 4.06 (d, J=5.31 Hz) 4.343 (t, J=5.13 Hz, 1H) 4.49 (t, J=5.13 Hz, 1H) 5.52 (s, 1H) 5.61 (s, 1H).

Example 43

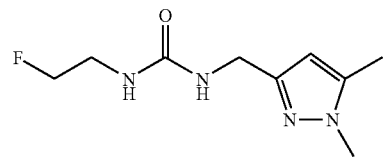

Synthesis of 1-(1,5-dimethyl-1H-pyrazol-3-ylmethyl)-3-(2-fluoro-ethyl)-urea (Compound 44)

The title compound was obtained from the commercially available 1,5-dimethyl-1H-pyrazol-3-yl)methylamine according to general procedure B described above.

1-(1,5-Dimethyl-1H-pyrazol-3-ylmethyl)-3-(2-fluoro-ethyl)-urea: The title compound was obtained from 1,5-dimethyl-1H-pyrazol-3-yl)methylamine (250 mg, 2.00 mmol), diimidazole carbonyl (323 mg, 1.99 mmol), fluoroethyl amine hydrochloride (220 mg, 90% purity, 1.99 mmol) and diisopropylethyl amine (0.7 mL, 4.02 mmol) according to the protocols as outlined in general procedure B above. Spectroscopic data: $^1$H NMR (300 MHz, Acetone-$d_6$) δ 2.22 (s, 3H) 3.38 (q, J=5.47 Hz, 1H) 3.46 (q, J=5.28 Hz, 1H) 3.68 (s, 3H) 4.18 (d, J=5.5 Hz) 4.34 (t, J=5.13 Hz, 1H) 4.50 (t, J=5.13 Hz, 1H) 5.82 (s, 1H) 5.89 (s, 1H), 5.92 (s, 1H).

Example 44

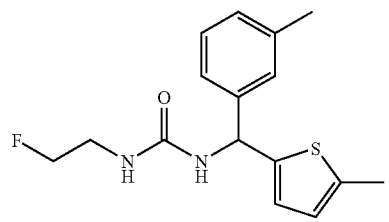 [SMILES: Cc1cccc(C(NC(=O)NCCF)c2ccc(C)s2)c1]

Synthesis of 1-(2-fluoro-ethyl)-3-[(5-methyl-thiophen-2-yl)-m-tolyl-methyl]-urea (Compound 34)

The desired starting amine was prepared from 5-methyl-thiophene-2-carboxylic acid according to the procedures shown in the scheme below. The title compound was thus obtained from this amine according to general procedure B described above.

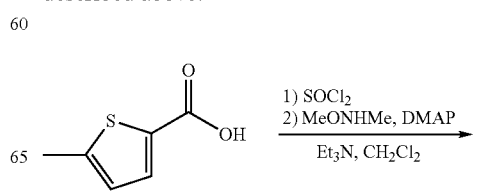

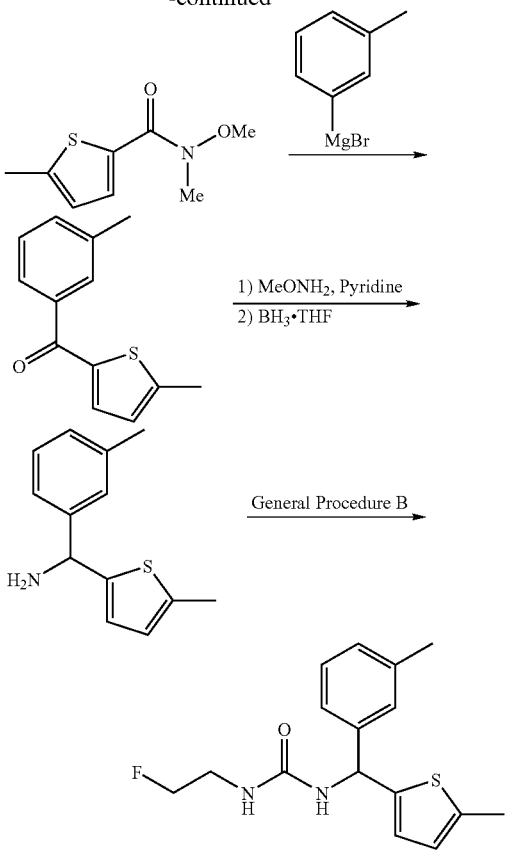

(5-Methyl-thiophen-2-yl)-m-tolyl-methanone: 5-Methyl-thiophene-2-carboxylic acid (25.00 g, 0.18 mol) was dissolved in benzene (150 mL), and sulfonyl chloride (30.00 mL, 0.41 mol) was added. The resulting reaction mixture was refluxed for 4 hours, then concentrated to afford the crude acid chloride. This crude acid chloride was then mixed in dichloromethane with N,O-dimethyl-hydroxylamine (1.3 eq) and a catalytic amount of DMAP and cooled to 0° C. Et$_3$N (4.0 eq) was added. The resulting mixture was stirred for 14 hours. Water was added to the reaction mixture, and the resulting mixture was extracted with EtOAc (3×200 mL). The combined organic extracts were washed with H$_2$O (2×200 mL) and brine (1×200 mL), then dried over MgSO$_4$ and concentrated to give the desired Weinreb's amide. This amide was then dissolved in THF at 0° C. and 3-methylphenylmagnesium bromide (1.5 eq) was added. The resulting mixture was stirred for 3 hours. It was quenched with 5% HCl and extracted with Et$_2$O (3×200 mL). The combined organic extracts were washed with H$_2$O (2×200 mL) and brine (1×200 mL), then dried over MgSO$_4$ and concentrated to give the crude ketone. The pure title ketone was obtained from column chromatography using hex:EtOAc (10:1) as the eluant. Spectroscopic data: $^1$H NMR (300 MHz, DMSO-d$_6$) δ ppm 2.38 (s, 3H) 2.54 (s, 3H) 6.91-7.05 (m, 1H) 7.06-7.29 (m, 1H) 7.37-7.49 (m, 2H) 7.50-7.68 (m, 2H).

C-(5-Methyl-thiophen-2-yl)-C-m-tolyl-methylamine: (5-Methyl-thiophen-2-yl)-m-tolyl-methanone (5.00 g, 23.12 mmol) was mixed with methoxylamine hydrochloride (3.00 g, 35.92 mmol) in pyridine and the resulting reaction mixture was stirred for 14 hours. The reaction mixture was concentrated on a rotary evaporator, the residue was washed with ether and the combined ether layers were concentrated. The residue was dissolved in BH$_3$.THF (100.00 mL, 1.0 M in THF, 0.10 mol) and the resulting mixture was refluxed for 3 hours. The reaction mixture was then cooled to 0° C., 20% NaOH was added and the resulting mixture was refluxed for 14 hours. After cooling to room temperature, the reaction mixture was extracted with hexane and the combined organic extracts were dried with K$_2$CO$_3$ and concentrated to give the desired title amine. Spectroscopic data: $^1$H NMR (300 MHz, DMSO-d$_6$) δ ppm 2.26 (s, 3H) 2.32 (s, 3H) 3.30 (br s, 2H) 5.14 (s, 1H) 6.48-6.58 (m, J=14.36 Hz, 1H) 6.58-6.67 (m, 1H) 6.93-7.08 (m, 1H) 7.11-7.27 (m, 3H).

1-(2-Fluoro-ethyl)-3((5-methyl-thiophen-2-yl)-m-tolyl-methyl)-urea: The title urea was obtained from C-(5-methyl-thiophen-2-yl)-C-m-tolyl-methylamine (crude, taken from the previous step), diimidazole carbonyl (1.62 g, 9.98 mmol), fluoroethyl amine hydrochloride (1.00 g, 90% purity, 9.05 mmol) and diisopropylethyl amine (3.60 mL, 20.67 mmol) according to the protocols as outlined in general procedure B above. Spectroscopic data: $^1$H NMR (300 MHz, DMSO-d) δ ppm 2.27 (s, 3H) 2.34 (s, 3H) 3.25 (q, J=5.08 Hz, 1H) 3.34 (q, J=4.98 Hz, 1H) 4.29 (t, J=4.98 Hz, 1H) 4.45 (t, J=4.98 Hz, 1H) 5.95 (d, J=8.79 Hz, 1H) 6.09-6.23 (m, 1H) 6.48-6.61 (m, 2H) 7.00 (d, J=8.50 Hz, 1H) 7.03-7.14 (m, 3H) 7.21 (t, J=7.33 Hz, 1H).

While this invention has been described with respect to these specific examples, it is understood that other modifications and variations are possible without departing from the spirit of the invention.

What is claimed is:

1. A compound having the structure:

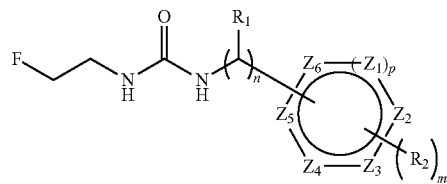

or a pharmaceutically acceptable salt thereof wherein:

R$_1$ is H, alkyl, phenyl, or substituted phenyl;

n is 0 or 1;

Z$_1$-Z$_6$ are each independently C, CH, N, O, or S;

p is 0 or 1;

m is 1 to 5;

each R$_2$ is independently lower alkyl, halide, trifluoromethyl, lower alkenyl, lower alkynyl, cycloalkyl, —CN, —CH$_2$CN, —CH$_2$SR$_3$, —CH$_2$N(R$^3$)$_2$, —CH$_2$OR$_3$, —OR$_3$, —SR$_3$, —C(O)R$_4$;

wherein two R$_2$ moieties taken together with carbon atoms to which each R$_2$ is attached may form an aryl, substituted aryl, heteroaryl, substituted heteroaryl, cycloalkyl, substituted cycloalkyl, heterocyclic, or substituted heterocyclic ring;

each R$_3$ is independently H, lower alkyl, or cycloalkyl; and each R$_4$ is independently H, lower alkyl, cycloalkyl, alkoxy, phenyl, substituted phenyl, heteroaryl, substituted heteroaryl, or trifluoromethyl.

2. The compound of claim 1, having any one of the structures:
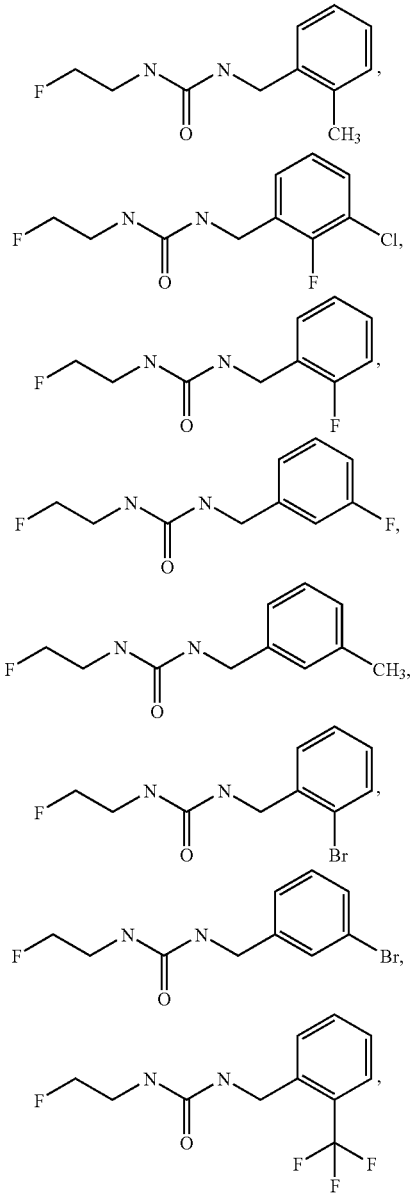
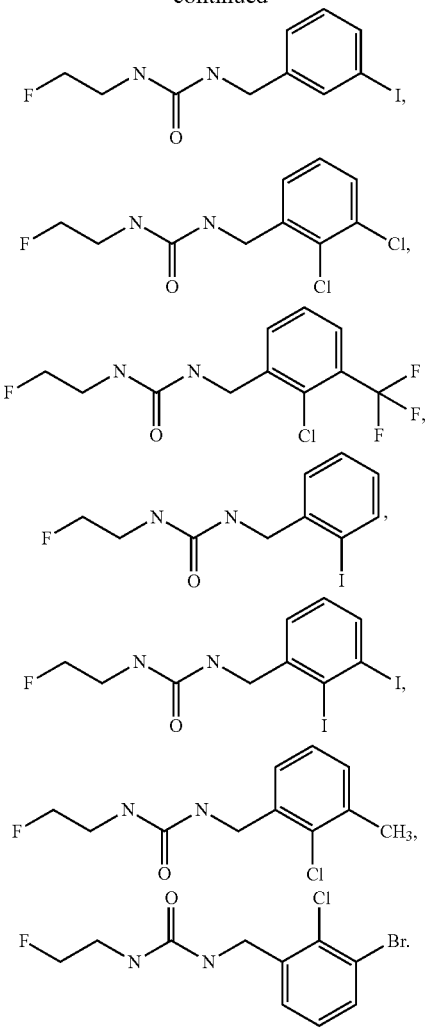
3. The compound of claim 1, wherein at least one of $Z_1$-$Z_6$ is N, O, or S.
4. The compound of claim 1, wherein $R_1$ is H.
5. The compound of claim 1, wherein $R_1$ is phenyl or substituted phenyl.
6. The compound of claim 1, wherein $R_1$ is alkyl.
* * * * *